US012685592B2

(12) United States Patent
Sakuragi

(10) Patent No.: US 12,685,592 B2
(45) Date of Patent: Jul. 21, 2026

(54) INCISION SIMULATION DEVICE, INCISION SIMULATION METHOD, AND PROGRAM

(71) Applicant: FUJIFILM Corporation, Tokyo (JP)

(72) Inventor: Futoshi Sakuragi, Tokyo (JP)

(73) Assignee: FUJIFILM Corporation, Tokyo (JP)

( * ) Notice: Subject to any disclaimer, the term of this patent is extended or adjusted under 35 U.S.C. 154(b) by 1109 days.

(21) Appl. No.: 17/697,902

(22) Filed: Mar. 17, 2022

(65) Prior Publication Data

US 2022/0313360 A1 Oct. 6, 2022

(30) Foreign Application Priority Data

Mar. 30, 2021 (JP) ................................ 2021-058615

(51) Int. Cl.

| | |
|---|---|
| ***A61B 34/10*** | (2016.01) |
| ***G06F 30/20*** | (2020.01) |
| ***G06T 15/08*** | (2011.01) |
| ***G06T 17/00*** | (2006.01) |

(52) U.S. Cl.

CPC .............. *A61B 34/10* (2016.02); *G06F 30/20* (2020.01); *G06T 15/08* (2013.01); *G06T 17/00* (2013.01); *A61B 2034/105* (2016.02); *A61B 2034/107* (2016.02)

(58) Field of Classification Search

CPC ................................ A61B 34/10; G06F 30/20

See application file for complete search history.

(56) References Cited

U.S. PATENT DOCUMENTS

| | | | | |
|---|---|---|---|---|
| 7,940,967 | B2 | 5/2011 | Ozaki et al. | |
| 8,466,916 | B2 | 6/2013 | Engel et al. | |
| 10,524,823 | B2 | 1/2020 | Sakuragi | |
| 2015/0133764 | A1* | 5/2015 | Sakuragi | A61B 6/032 600/407 |

FOREIGN PATENT DOCUMENTS

| | | |
|---|---|---|
| JP | 2003010172 | 1/2003 |
| JP | 2005278888 | 10/2005 |
| JP | 2007222629 | 9/2007 |
| JP | 2008167793 | 7/2008 |
| JP | 2014018619 | 2/2014 |

OTHER PUBLICATIONS

Shi, W., Liu, P. X., & Zheng, M. (2020). Cutting procedures with improved visual effects and haptic interaction for surgical simulation systems. Computer Methods and Programs in Biomedicine, 184, 105270. (Year: 2020).*

(Continued)

*Primary Examiner* — Bijan Mapar
(74) *Attorney, Agent, or Firm* — JCIPRNET

(57) ABSTRACT

An incision simulation device includes a processor, in which the processor acquires an incision line for a three-dimensional organ image showing an organ which is an incision simulation target, and specifies an incision region from the three-dimensional organ image based on an incision process position between the incision line and a maximum incision region, first distance data with the incision line as a reference, and second distance data with the maximum incision region designated for the three-dimensional organ image as a reference.

11 Claims, 19 Drawing Sheets

(56) References Cited

OTHER PUBLICATIONS

"Office Action of Japan Counterpart Application", issued on Aug. 20, 2024, with English translation thereof, pp. 1-3.

Yuya Oda, "Visualizing the Organ Resection process for Hepatectomy Support", Master's Thesis, Graduate School of Information Science, Division of Information Biology, Nara Institute of Science and Technology, Mar. 6, 2012, with English translation thereof, pp. 1-78.

Megumi Nakao, "Real-time vol. Graphics", Medical Imaging Technology, vol. 25 No. 3, May 2007, with English translation thereof, pp. 1-12.

* cited by examiner

10
MEDICAL SERVICE SUPPORT DEVICE
12
IMAGE PROCESSING DEVICE
24
PROCESSOR
26
STORAGE
28
RAM
30
COMMUNICATION I/F
34
32
EXTERNAL I/F
16
DISPLAY
14
RECEPTION DEVICE

10
MEDICAL SERVICE SUPPORT DEVICE
26
STORAGE
36
INCISION SIMULATION PROCESSING PROGRAM
28
RAM
24
PROCESSOR
INCISION SIMULATION PROCESSING
EXTRACTION UNIT
RENDERING UNIT
CONTROLLER
INCISION PARAMETER ACQUISITION UNIT
INCISION MAXIMUM AMOUNT CALCULATION UNIT
MAXIMUM INCISION REGION SPECIFYING UNIT
INCISION REGION SPECIFYING UNIT
24A
24B
24C
24D
24E
24F
24G

RENDERING UNIT
24B
42
44
46
48
48
50
50
50
50

RENDERING IMAGE
46
PROJECTION PLANE
44
ACCUMULATE VOXEL DATA
V
DESIGNATED VOXEL
42
50
48

Figure 15:
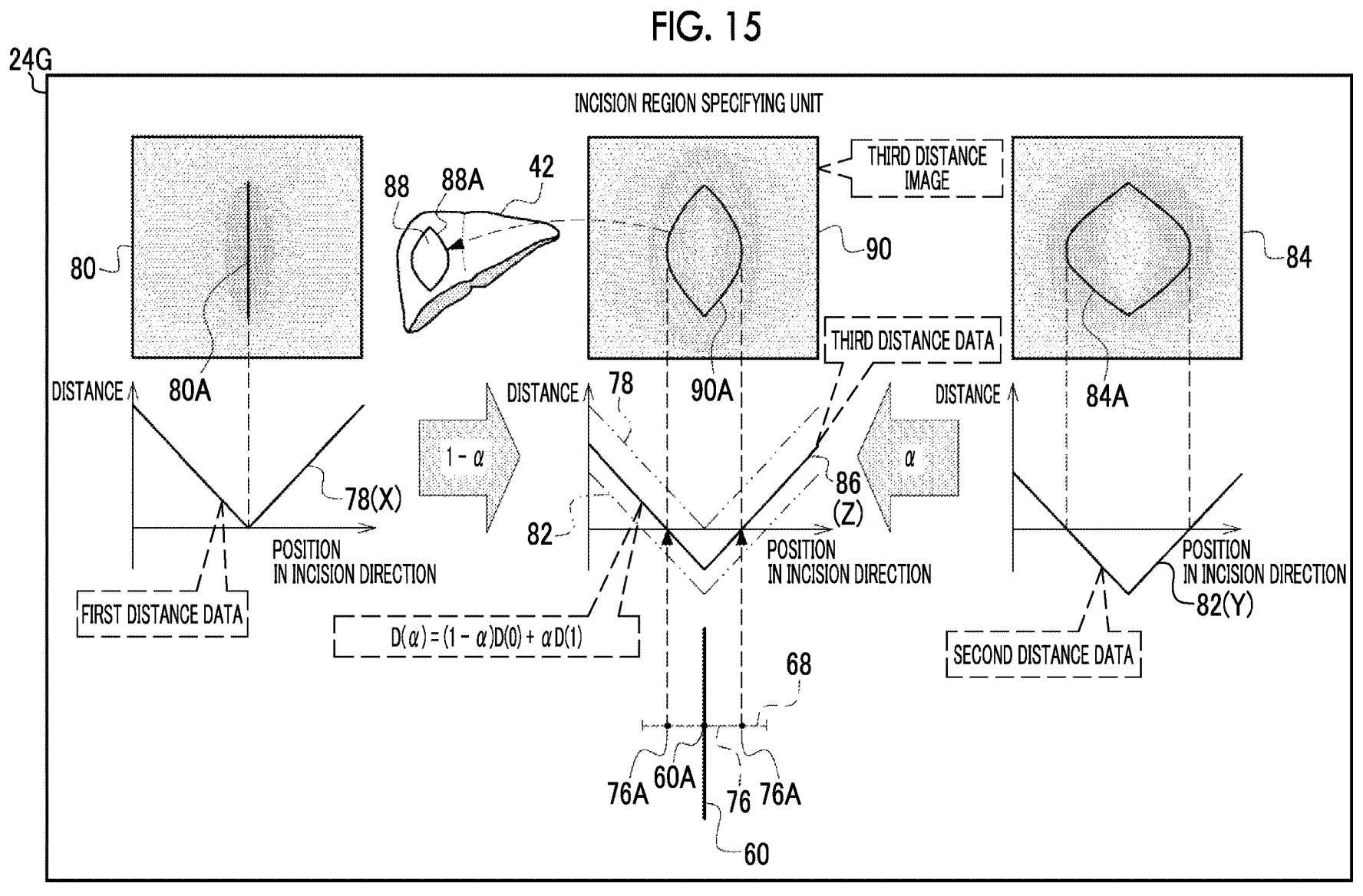

INCISION REGION SPECIFYING UNIT

THIRD DISTANCE IMAGE

THIRD DISTANCE DATA

SECOND DISTANCE DATA

FIRST DISTANCE DATA

DISTANCE

POSITION IN INCISION DIRECTION $D(\alpha) = (1-\alpha)D(0) + \alpha D(1)$ $\alpha$ $1-\alpha$ 80 80A 78(X) 88 88A 42 90 90A 86 (Z) 78 82 84 84A 82(Y) 68 76 76A 60 60A

FIG. 19

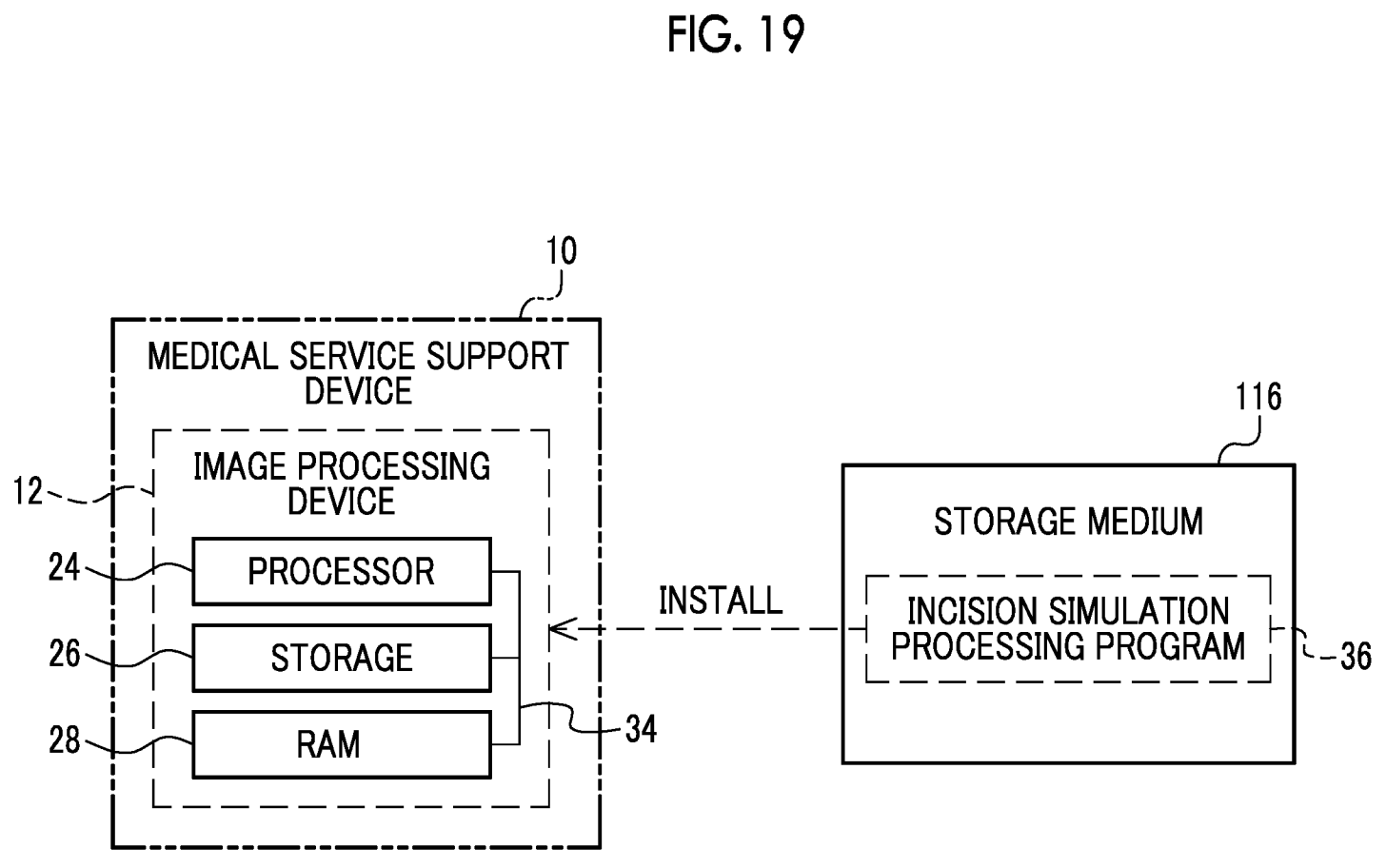

10
MEDICAL SERVICE SUPPORT DEVICE
IMAGE PROCESSING DEVICE
PROCESSOR
STORAGE
RAM
12
24
26
28
34
INSTALL
116
STORAGE MEDIUM
INCISION SIMULATION PROCESSING PROGRAM
36

INCISION SIMULATION DEVICE, INCISION SIMULATION METHOD, AND PROGRAM

CROSS-REFERENCE TO RELATED APPLICATIONS

The present application claims priority under 35 U.S.C. § 119 to Japanese Patent Application No. 2021-058615 filed on Mar. 30, 2021. Each of the above application is hereby expressly incorporated by reference, in its entirety, into the present application.

BACKGROUND OF THE INVENTION

1. Field of the Invention

The technology of the present disclosure relates to an incision simulation device, an incision simulation method, and a program.

2. Description of the Related Art

JP2007-222629A discloses a method of volume rendering a digitized medical image including the steps of: providing a digitized medical image volume, the image including a plurality of intensities represented as a three-dimensional grid of points; providing a projection plane including a two-dimensional lattice of points onto which rendering radiation is projected from a view point through the image volume; advancing a sampling point along radiation through the image volume; creating an incision region within the image volume; determining whether the sampling point is within the incision region, in which a first transfer function is applied to a sample value interpolated from a first volume in a case in which the sampling point is within the incision region, and a second transfer function is applied to a sample value interpolated from a second volume in a case in which the sampling point is outside the incision region; and accumulating the output of the transfer function.

JP2014-018619A discloses a surgery support apparatus comprising: an image generation unit that generates, from a three-dimensional image of an organ in which an excision region has been specified, an image representing the organ in such a manner that a blood vessel region in the organ is visually recognizable; a depth input receiving unit that receives an input designating a depth of cutting; and a cut surface setting unit that determines, as a cut surface, a portion of a boundary surface within the designated depth of cutting along the boundary surface from an outer edge of the boundary surface toward an inside, and the boundary surface being between the excision region and a non-excision region, which is a region other than the excision region, in the organ, in which the image generation unit generates, from the three-dimensional image, the image representing the organ in such a manner that only a partial blood vessel region, which is present in a neighborhood region of the cut surface in the blood vessel region of the organ, is visually recognizable.

JP2008-167793A discloses a surgery support method of providing a surgery support through a medical image of a subject displayed on a display, the method including creating an image simulating a spread state of a cut surface by a surgical instrument from three-dimensional image data of the subject and displaying the created image.

SUMMARY OF THE INVENTION

One embodiment according to the technology of the present disclosure provides an incision simulation device, an incision simulation method, and a program which can reduce a load on an operation relating to an incision region as compared to a case in which the operation relating to the incision region is followed and executed as the incision region is gradually expanded.

A first aspect of the technology of the present disclosure relates to an incision simulation device comprising a processor, in which the processor acquires an incision line for a three-dimensional organ image showing an organ which is an incision simulation target, and specifies an incision region from the three-dimensional organ image based on an incision process position between the incision line and a maximum incision region, first distance data with the incision line as a reference, and second distance data with the maximum incision region designated for the three-dimensional organ image as a reference.

A second aspect of the technology of the present disclosure relates to an incision simulation method comprising acquiring an incision line for a three-dimensional organ image showing an organ which is an incision simulation target, and specifying an incision region from the three-dimensional organ image based on an incision process position between the incision line and a maximum incision region, first distance data with the incision line as a reference, and second distance data with the maximum incision region designated for the three-dimensional organ image as a reference.

A third aspect of the technology of the present disclosure relates to a program causing a computer to execute a process comprising acquiring an incision line for a three-dimensional organ image showing an organ which is an incision simulation target, and specifying an incision region from the three-dimensional organ image based on an incision process position between the incision line and a maximum incision region, first distance data with the incision line as a reference, and second distance data with the maximum incision region designated for the three-dimensional organ image as a reference.

BRIEF DESCRIPTION OF THE DRAWINGS

FIG. 15 is a conceptual diagram showing an example of a processing content in which an incision region is specified from the three-dimensional organ image.

FIG. 19 is a block diagram showing an example of an aspect in which an image generation output processing program stored in a storage medium is installed in the image processing device.

DESCRIPTION OF THE PREFERRED EMBODIMENTS

An example of an embodiment of an incision simulation device, an incision simulation method, and a program according to the technology of the present disclosure will be described with reference to the accompanying drawings.

Figure 1:
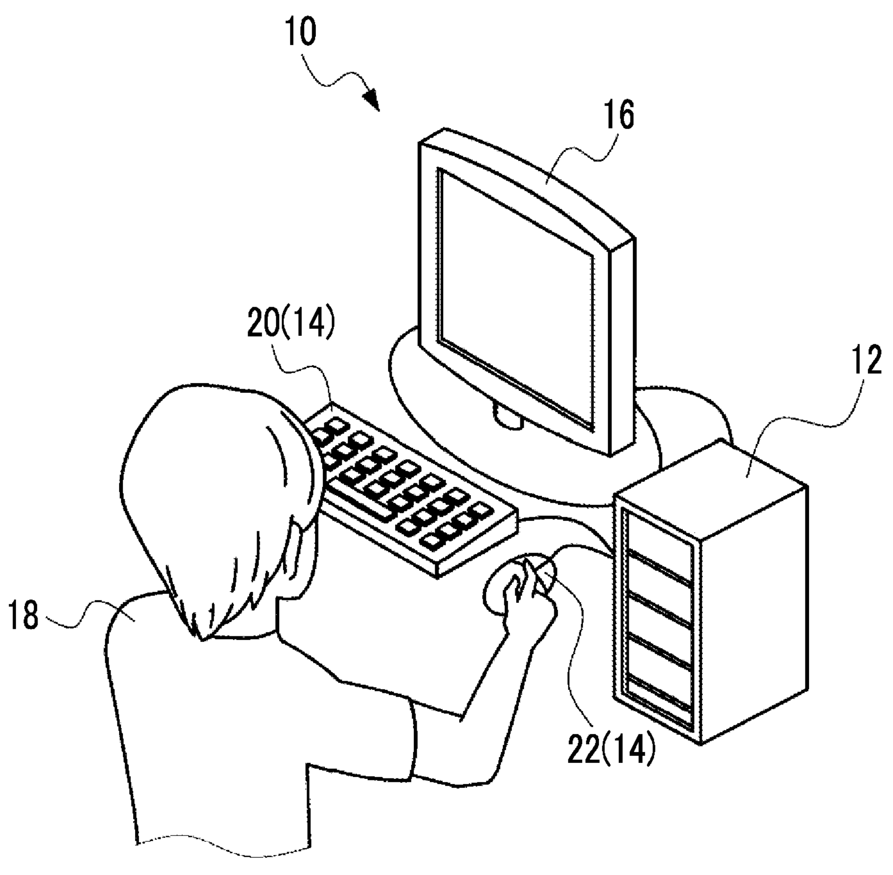
FIG. 1 is a conceptual diagram showing a schematic configuration of a medical service support device.

As shown in FIG. 1 as an example, a medical service support device 10 comprises an image processing device 12, a reception device 14, and a display 16, and is used by a user 18. Here, examples of the user 18 include a doctor and a technician.

The reception device 14 is connected to the image processing device 12. The reception device 14 includes a keyboard 20, a mouse 22, and the like, and receives an instruction from the user 18. In the example shown in FIG. 1, the keyboard 20 and the mouse 22 are shown as the reception device 14, but the keyboard 20 and the mouse 22 are merely examples, and a touch panel and/or a tablet may be used instead of the keyboard 20 and/or the mouse 22, or together with the keyboard 20 and/or the mouse 22. At least one of the keyboard 20, the mouse 22, the touch panel or the tablet that receives proximity input, a voice input device that receives voice input, an imaging apparatus that receives gesture input, or a sensor may be used as the reception device 14. In addition, the connection between the reception device 14 and the image processing device 12 may be wired or wireless.

The display 16 is connected to the image processing device 12. Examples of the display 16 include an electro-luminescence (EL) display, and a liquid crystal display. The display 16 displays various pieces of information (for example, an image and a text) under the control of the image processing device 12.

Figure 2:
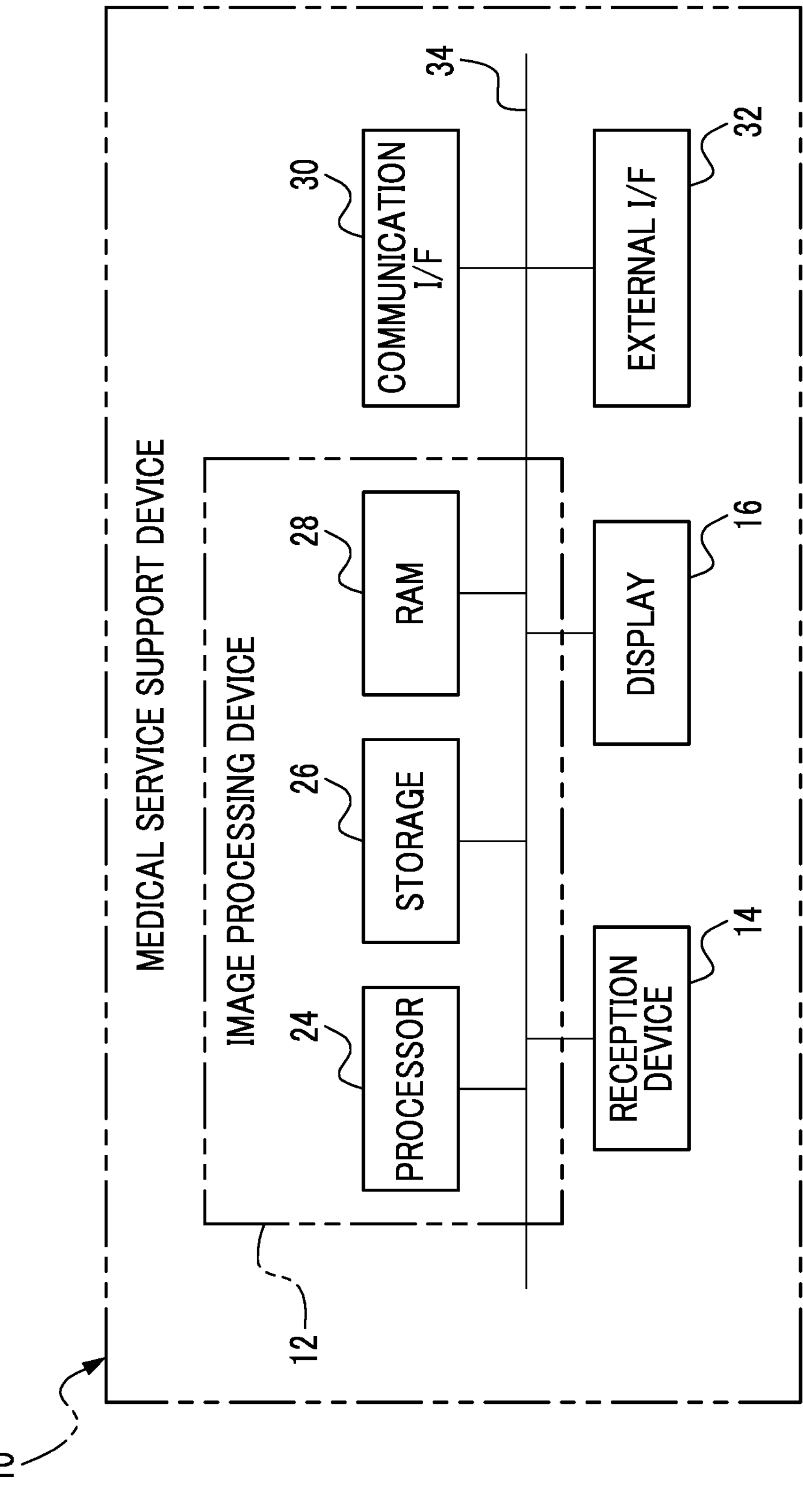
FIG. 2 is a block diagram showing an example of a hardware configuration of an electric system of the medical service support device.

As shown in FIG. 2 as an example, the medical service support device 10 comprises a communication interface (I/F) 30, an external I/F 32, and a bus 34 in addition to the image processing device 12, the reception device 14, and the display 16.

The image processing device 12 is an example of an "incision simulation device" and a "computer" according to the technology of the present disclosure, and comprises a processor 24, a storage 26, and a random access memory (RAM) 28. The processor 24, the storage 26, the RAM 28, the communication I/F 30, and the external I/F 32 are connected to the bus 34.

A memory is connected to the processor 24. The memory includes the storage 26 and the RAM 28. The processor 24 includes a central processing unit (CPU) and a graphics processing unit (GPU). The GPU is operated under the control of the CPU and is responsible for executing processing relating to the image. Examples of the processing relating to the image include incision simulation processing (see FIGS. 3 and 17) described below.

The storage 26 is a non-volatile storage device that stores various programs, various parameters, and the like. Examples of the storage 26 include a hard disk drive (HDD) and a solid state drive (SSD). Note that the HDD and the SSD are merely examples, and at least one of the HDD, the SSD, a flash memory, a magnetoresistive memory, or a ferroelectric memory may be used as the storage 26.

The RAM 28 is a memory in which information is transitorily stored, and is used as a work memory by the processor 24. Examples of the RAM 28 include a dynamic random access memory (DRAM) and a static random access memory (SRAM).

The communication I/F 30 is connected to a network (not shown). The network may be configured by at least one of a local area network (LAN) or a wide area network (WAN), for example. An external device (not shown) or the like is connected to the network, and the communication I/F 30 controls the exchange of the information with and from an external communication apparatus via the network. The external communication apparatus may include, for example, at least one of a magnetic resonance imaging (MRI) apparatus, a personal computer, or a smart device. For example, the communication I/F 30 transmits the information in response to a request from the processor 24 to the external communication apparatus via the network. In addition, the communication I/F 30 receives the information transmitted from the external communication apparatus, and outputs the received information to the processor 24 via the bus 34.

The external I/F 32 controls the exchange of various pieces of information with and from an external device (not shown) present outside the medical service support device 10. The external device may be, for example, at least one of a smart device, a personal computer, a server, a universal serial bus (USB) memory, a memory card, or a printer. Examples of the external I/F 32 include a USB interface. The external device is directly or indirectly connected to the USB interface.

By the way, before the surgery to remove a malignant tumor, such as lung cancer and/or liver cancer, from the organ, increasing the safety of the surgery is performed by deciding and planning an excision region before the surgery by using a plurality of two-dimensional slice images obtained by imaging a patient who is a subject by the modality, such as a computed tomography (CT) apparatus and/or a magnetic resonance imaging (MRI) apparatus.

However, in reality, the surgery is performed while gradually incising the excision region from the planned incision line, but for the simulation of a situation in which the incision and opening are partially performed, there are many surgery simulations using a surface model using a patient standard model. In a case in which the plurality of two-dimensional slice images relating to an actual patient in the surgery simulation using the surface model, it is necessary to extract an organ image or the like showing the organ from the plurality of two-dimensional slice images to create a three-dimensional image. In a case in which the three-dimensional organ image is created by extracting the organ image or the like, there are a problem that it takes a lot of time and effort, and a problem that the volume data needs to be deformed and the calculation cost is high in a case in which the plurality of two-dimensional slice images are to be used as they are.

Regarding the former problem, the time and effort can be minimized by automating the extraction of the organ images or the like with the surgery planning software described above, but for the latter problem, the technology of reducing the calculation cost as much as possible is needed.

As the technology of reducing the calculation cost, the technology of performing rendering in consideration of the deformation in a case of volume rendering (hereinafter, referred to as "rendering") without deforming the three-dimensional organ image which is the volume data (see "Real-time Volume Graphics", Nakao, MEDICAL IMAGING TECHNOLOGY Vol. 25, No. 3, May 2007) has been known. However, in a case in which the incision is simulated, it is necessary to represent a blank space in the incision in addition to the deformation. A method of representing the blank space has also been proposed (see "Visualizing organ resection procedures to support hepatectomy", Oda, Nara Institute of Science and Technology, thesis for master degree, NAIST-IS-MT1051024, 2012). However, the method has the calculation cost of having to calculate the blank space each time the incision is gradually performed.

Figure 3:
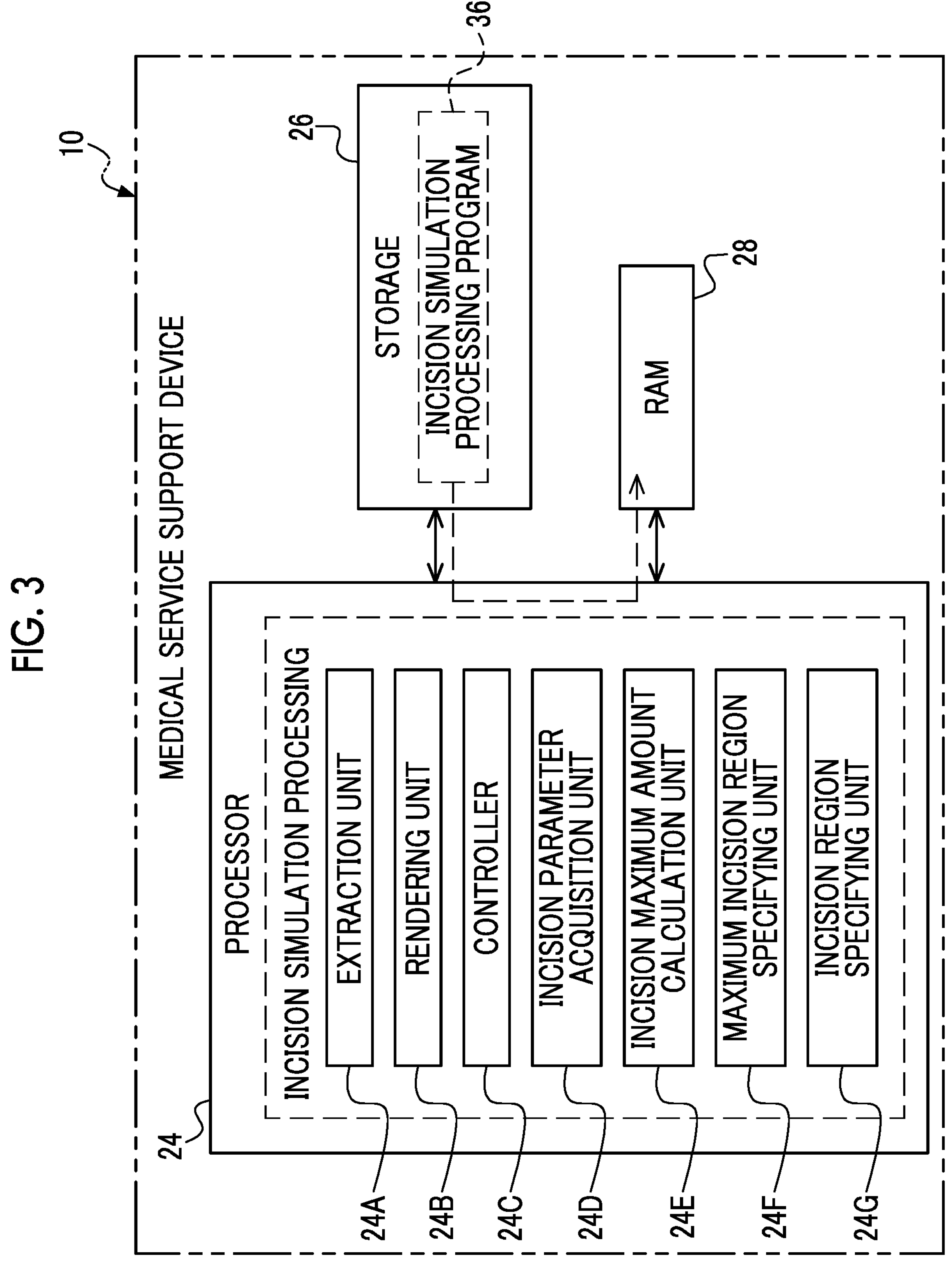
FIG. 3 is a block diagram showing an example of a main function of an image processing device provided in the medical service support device.

Therefore, in the present embodiment, the incision simulation processing is performed by the processor 24 as shown in FIG. 3 as an example such that the incision simulation can be performed more smoothly by further reducing the calculation cost in a case in which the incision process is simulated. An incision simulation processing program 36 is stored in the storage 26. The processor 24 reads out the incision simulation processing program 36 from the storage 26 and executes the read out incision simulation processing program 36 on the RAM 28 to perform the incision simulation processing. The incision simulation processing is realized by the processor 24 operated as an extraction unit 24A, a rendering unit 24B, a controller 24C, an incision parameter acquisition unit 24D, an incision maximum amount calculation unit 24E, a maximum incision region specifying unit 24F, and an incision region specifying unit 24G. Note that the incision simulation processing program 36 is an example of a "program" according to the technology of the present disclosure.

Figure 4:
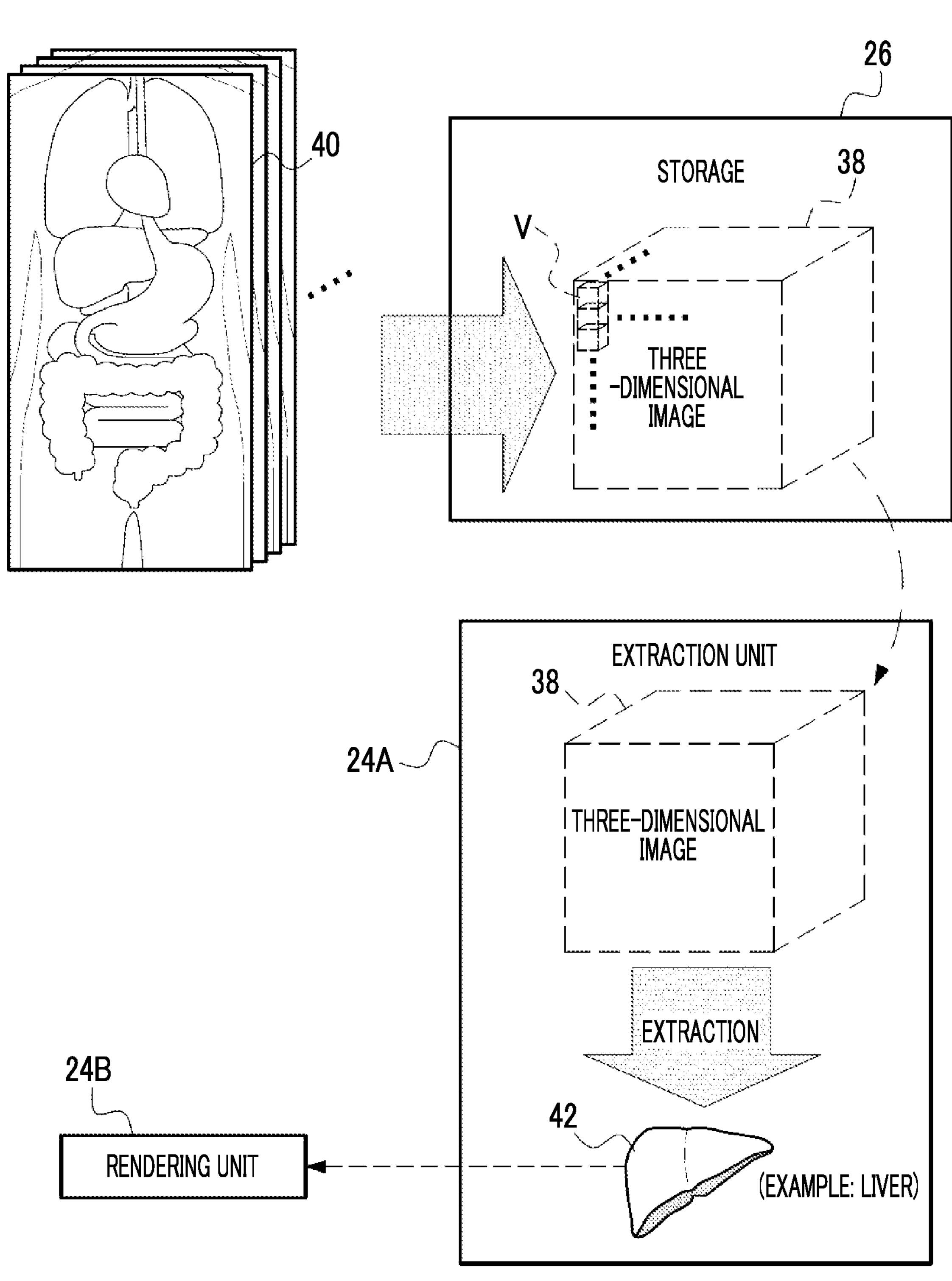
FIG. 4 is a conceptual diagram showing an example of a processing content of an extraction unit.

As shown in FIG. 4 as an example, a three-dimensional image 38 is stored in the storage 26. The three-dimensional image 38 is an image obtained by stacking a plurality of two-dimensional slice images 40 obtained by imaging the patient by the modality and dividing the stacked two-dimensional slice images 40 into a voxel V. Examples of the modality include the CT apparatus. The CT apparatus is merely an example, and other examples of the modality include the MRI apparatus and an ultrasound diagnostic apparatus. In addition, in the example shown in FIG. 4, the two-dimensional slice image of a coronal plane is shown as the two-dimensional slice image 40, but the technology of the present disclosure is not limited to this, and a two-dimensional slice image of a cross section may be used, or a two-dimensional slice image of an arrow surface may be used. Each position of all voxels V defining the three-dimensional image is specified in a three-dimensional coordinate. Non-transparency, color information of red (R), green (G), and blue (B), brightness, and the like (hereinafter, these are also referred to as "voxel data") are given to each voxel V.

The extraction unit 24A acquires the three-dimensional image 38 from the storage 26, and extracts a three-dimensional organ image 42 from the acquired three-dimensional image 38. The three-dimensional organ image 42 is the three-dimensional image showing the organ. For example, the three-dimensional image 38 includes a plurality of the three-dimensional organ images 42, and a unique identifier is given to each three-dimensional organ image 42. The three-dimensional organ image 42 is extracted from the three-dimensional image 38 in response to the instruction received by the reception device 14. For example, the extraction unit 24A extracts the three-dimensional organ image 42 corresponding to the identifier received by the reception device 14 from the three-dimensional image 38. In the example shown in FIG. 4, an image showing a liver is shown as an example of the three-dimensional organ image 42.

Note that, here, as an example of the three-dimensional organ image 42, the image showing the liver is described, but this is merely an example, and an image showing another organ, such as a heart and/or lungs, may be used. In addition, the method of extracting the three-dimensional organ image 42 by using the unique identifier is merely an example, and it suffices to extract, by the extraction unit 24A, the three-dimensional organ image 42 designated by the user 18 by any method via the reception device 14.

The rendering unit 24B renders the three-dimensional organ image 42 on a projection plane 44 corresponding to a screen of the display 16 by performing ray casting. A rendering image 46 is projected on the projection plane 44.

The projection plane 44 is, for example, a virtual plane defined by a resolution corresponding to a resolution of the screen of the display 16. The ray casting is performed by the rendering unit 24B, so that a virtual ray 50 passes through the three-dimensional organ image 42 from each viewpoint 48 corresponding to each pixel (that is, the pixel) of the projection plane 44, and is projected on the projection plane 44. The position of each viewpoint 48 with respect to the three-dimensional organ image 42 is changed, for example, in response to the instruction received by the reception device 14, so that the rendering image 46 in a case in which the three-dimensional organ image 42 is observed from various directions is projected on the projection plane 44. Note that the rendering image 46 projected on the projection plane 44 is, for example, displayed on the display 16 or stored in a predetermined storage device (for example, the storage 26).

Figure 6:
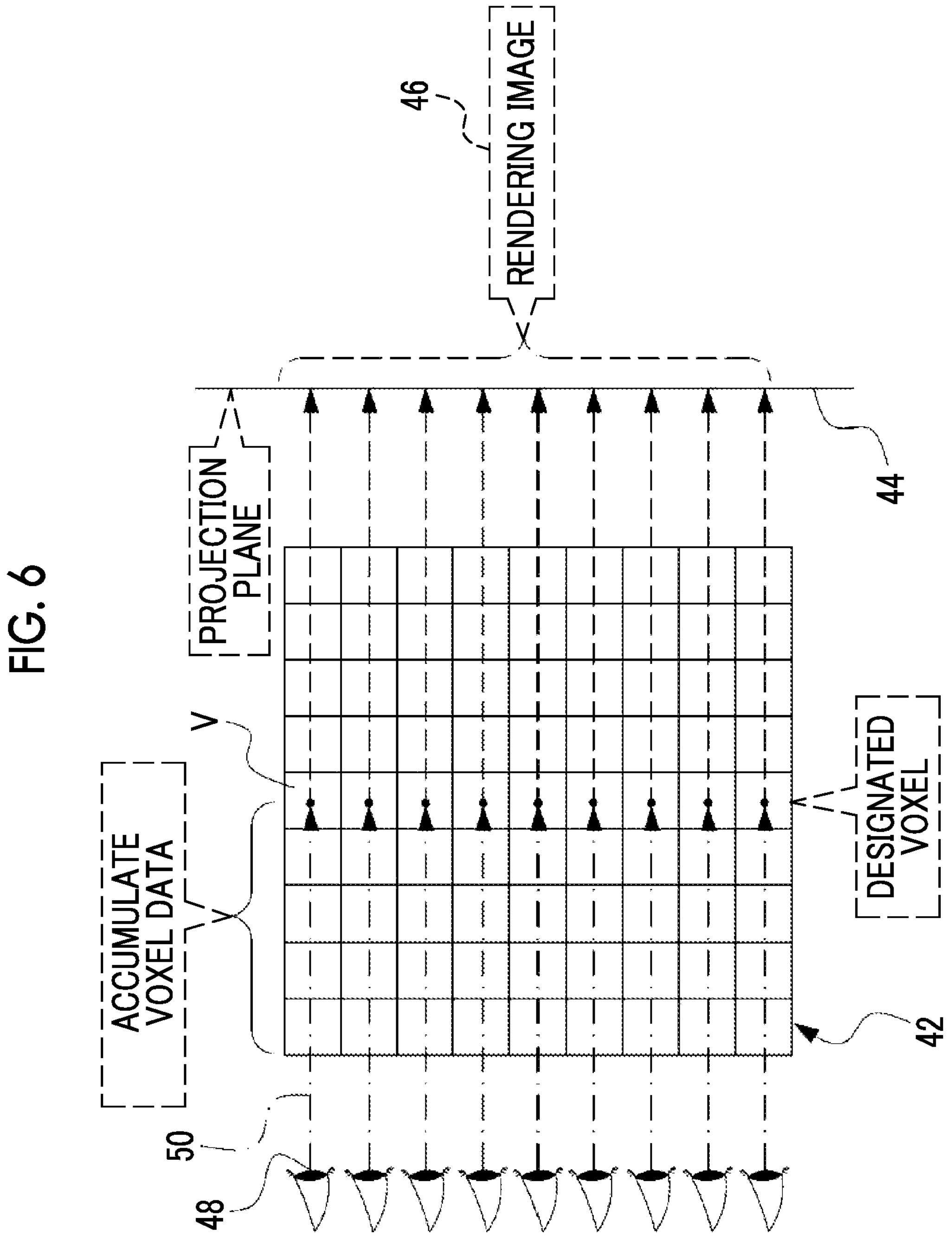
FIG. 6 is a conceptual diagram showing an example of an aspect in which rendering is performed with respect to a three-dimensional organ image.

As shown in FIG. 6 as an example, the ray 50 projects data (hereinafter, also referred to as "accumulation data") obtained by accumulating the voxel data obtained by a sampling point (for example, a point defined by one voxel interval) to a designated voxel, that is, the voxel V at a designated position on the projection plane 44 while passing through the three-dimensional organ image 42. As a result, the accumulation data is given to each pixel of the projection plane 44 as a pixel value. The rendering unit 24B generates the rendering image 46 according to the accumulation data given to each pixel.

Figure 7:
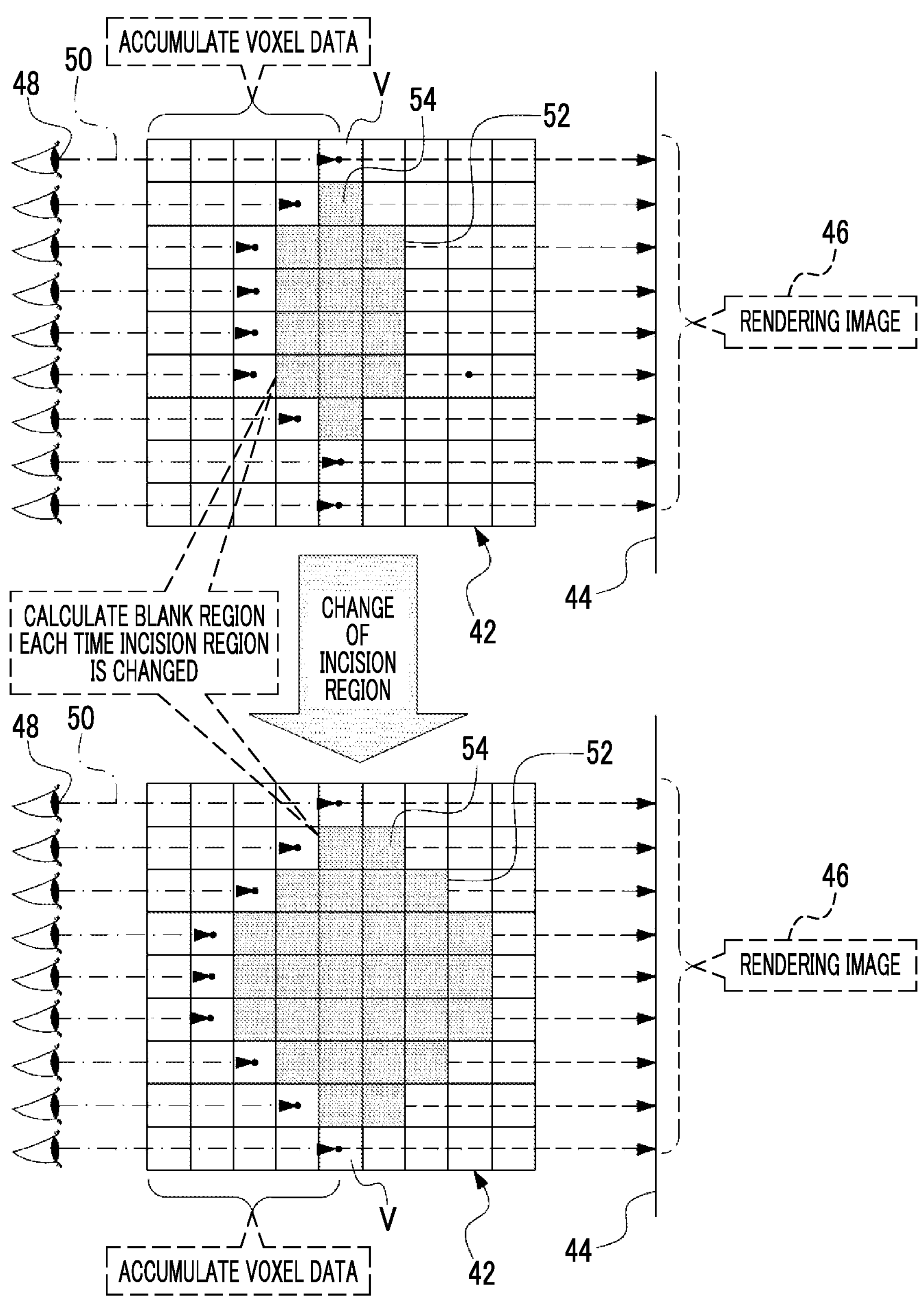
FIG. 7 is a conceptual diagram showing an example of an aspect in which an incision region set for the three-dimensional organ image is changed.

By the way, in a case in which the rendering unit 24B generates the rendering image 46 showing an aspect in the incision region set for the three-dimensional organ image 42, the calculation of the blank region generated inside the incision region (for example, the calculation of the position and the size of the blank region) is required. However, as shown in FIG. 7 as an example, in a case in which an incision region 52 set for the three-dimensional organ image 42 is changed, the calculation of a blank region 54 generated by the incision region 52 is required each time the incision region 52 is changed, and the load on the calculation is increased as compared to a case in which the blank region 54 is calculated only once. Therefore, in the present embodiment, the processor 24 performs the processing shown in FIGS. 8 to 16 as an example.

Figure 8:
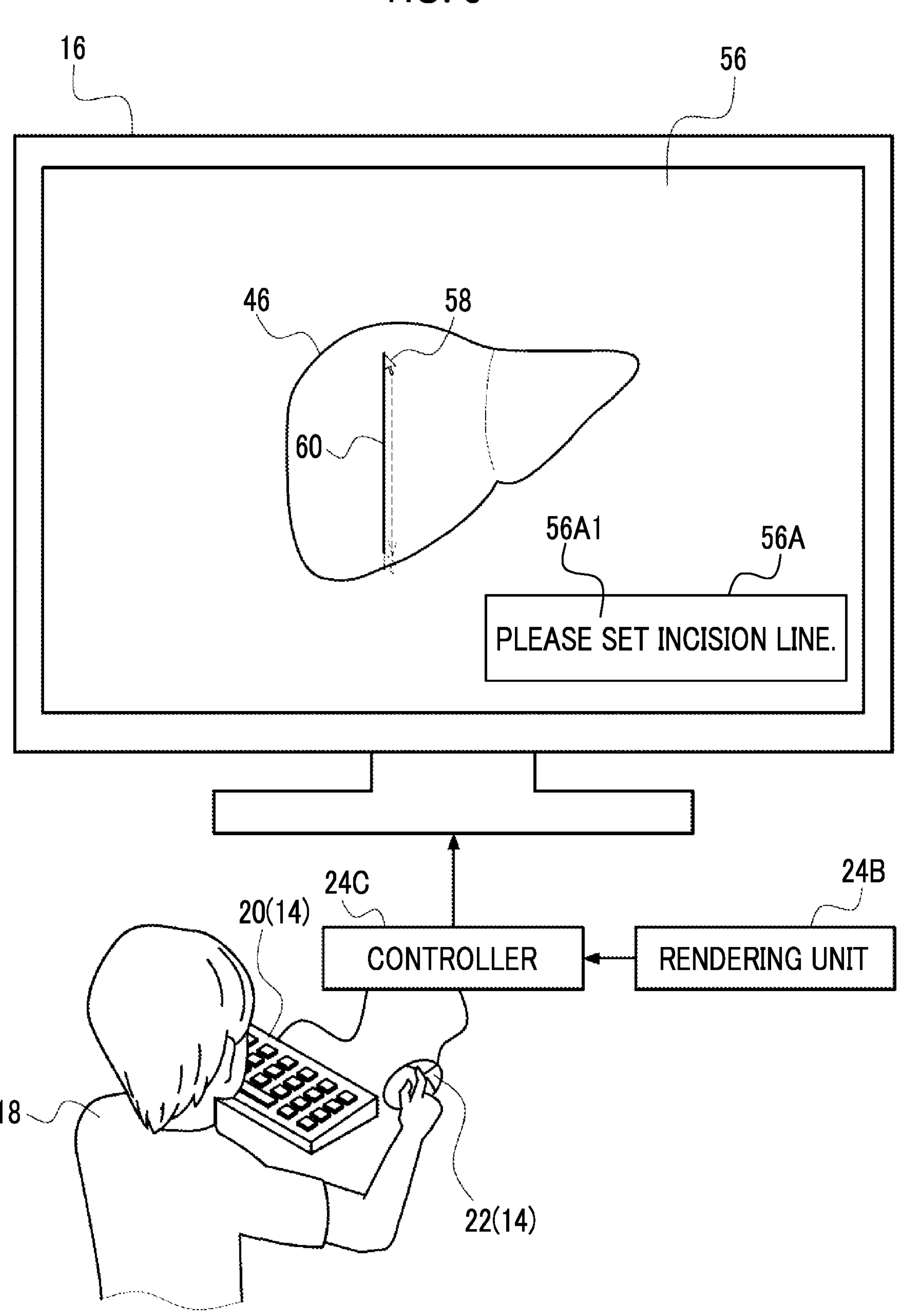
FIG. 8 is a conceptual diagram showing an example of an aspect in which an incision line is set.

As shown in FIG. 8 as an example, the controller 24C controls a graphical user interface (GUI) in response to the instruction received by the reception device 14 to display a screen 56 on the display 16. In addition, the controller 24C makes various settings in response to the instructions received by the reception device 14.

The rendering image 46 generated by the rendering unit 24B is displayed on the screen 56. The screen 56 includes a guide message display region 56A. A guide message 56A1 is displayed in the guide message display region 56A. The guide message 56A1 is a message that guides the user 18 to set an incision line 60 for the three-dimensional organ image 42 (see FIGS. 4 to 7) via the rendering image 46. In the example shown in FIG. 8, a message "Please set the incision line." is shown as an example of the guide message 56A1.

A pointer 58 is displayed on the screen 56. The user 18 sets the incision line 60 for the rendering image 46 by operating the pointer 58 via the reception device 14 (here, for example, the mouse 22). In the example shown in FIG. 8, a linear line is shown as an example of the incision line 60 formed for the rendering image 46 by operating the pointer 58. The incision line 60 formed for the rendering image 46 is confirmed in response to the instruction received by the reception device 14.

Figure 9:
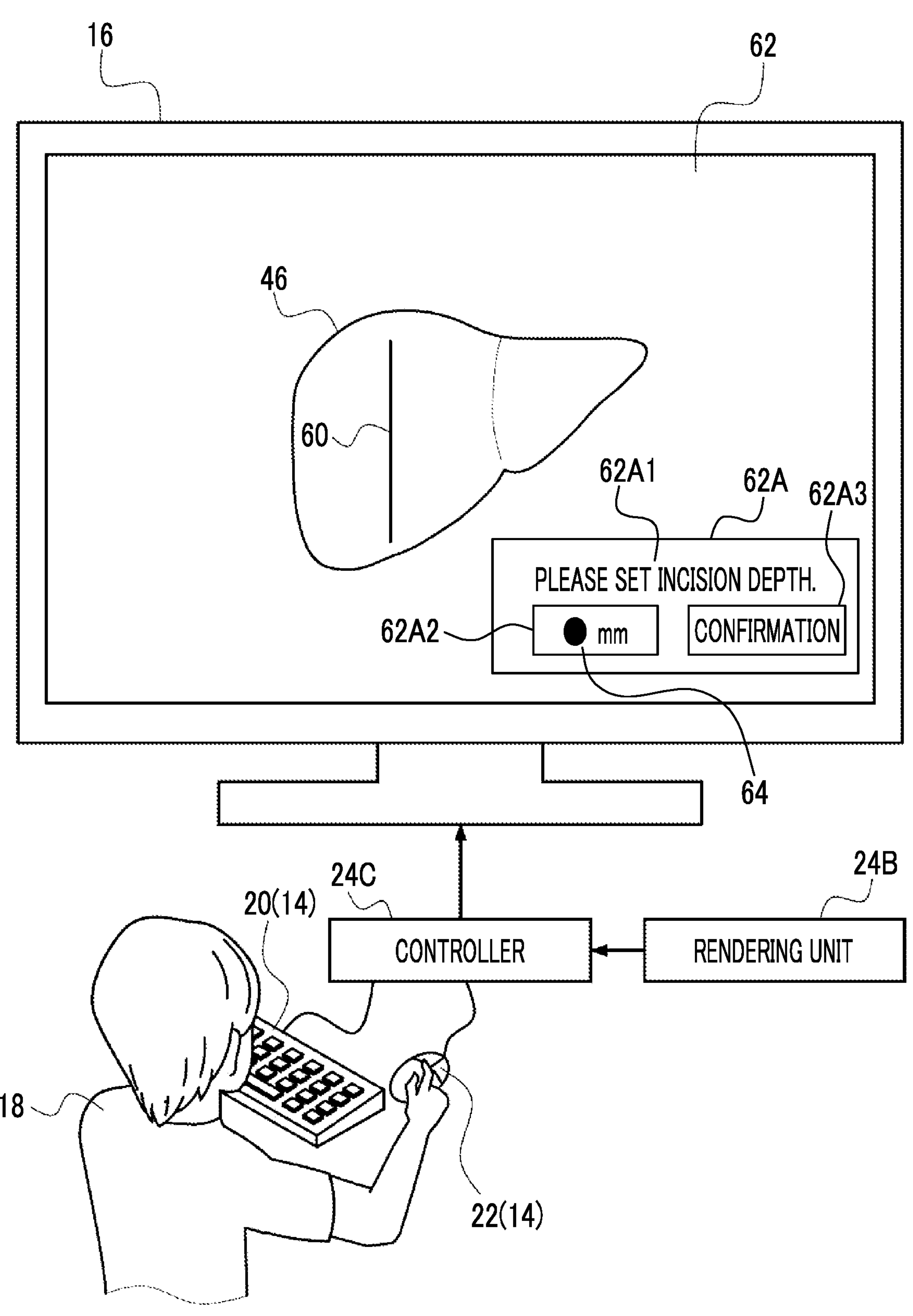
FIG. 9 is a conceptual diagram showing an example of an aspect in which an incision depth is set.

In a case in which the setting of the incision line 60 is terminated, as shown in FIG. 9 as an example, the screen displayed on the display 16 is switched from the screen 56 to a screen 62 by the controller 24C. The rendering image 46 on which the incision line 60 is drawn is displayed on the screen 62. In addition, the screen 62 includes a depth setting box 62A. The depth setting box 62A includes a guide message 62A1, an input box 62A2, and a confirmation key 62A3.

The guide message 62A1 is a message that guides the user 18 to set an incision depth 64 (hereinafter, also simply referred to as a "depth 64") for the three-dimensional organ image 42 (see FIGS. 4 to 7). In the example shown in FIG. 9, a message "Please set the incision depth." is shown.

The input box 62A2 is a box to which the depth 64 is input. For example, the depth 64 is input to the input box 62A2 as a numerical value in millimeters. The user 18 inputs the depth 64 to the input box 62A2 via the reception device 14 (here, for example, the keyboard 20).

The confirmation key 62A3 is a soft key that is turned on in a case in which the depth 64 input to the input box 62A2 is confirmed. In a case in which the depth 64 is input to the input box 62A2, the user 18 turns on the confirmation key 62A3 via the reception device 14 (here, for example, the mouse 22). As a result, the depth 64 input to the input box 62A2 is confirmed.

Figure 10:
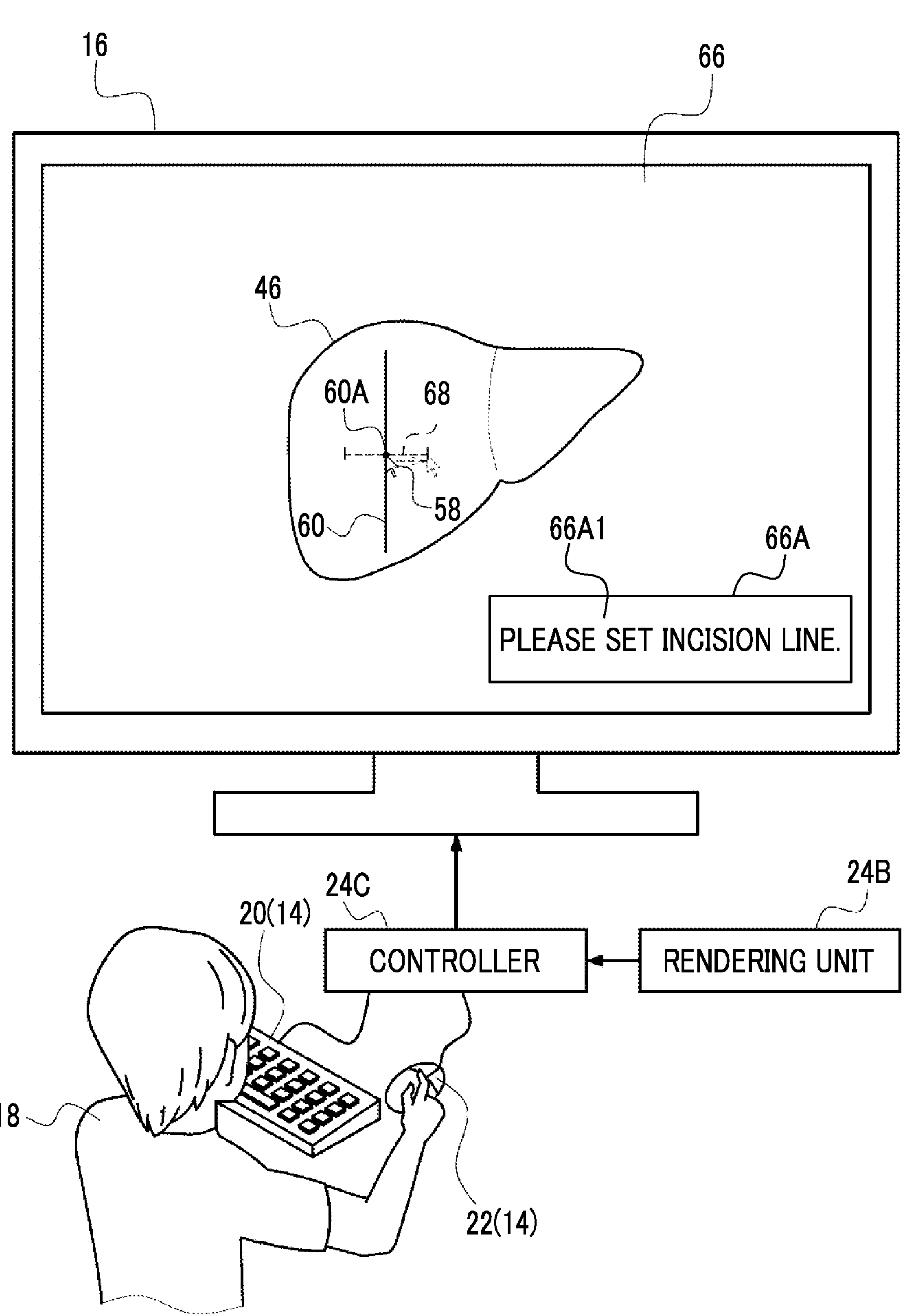
FIG. 10 is a conceptual diagram showing an example of an aspect in which an incision width is set.

In a case in which the setting of the depth 64 is terminated, as shown in FIG. 10 as an example, the screen displayed on the display 16 is switched from the screen 62 to a screen 66 by the controller 24C. The screen 66 includes a guide message display region 66A. A guide message 66A1 is displayed in the guide message display region 66A. The guide message 66A1 is a message that guides the user 18 to set an incision width 68 for the three-dimensional organ image 42 (see FIGS. 4 to 7) via the rendering image 46. In the example shown in FIG. 10, a message "Please set the incision width." is shown as an example of the guide message 66A1.

The incision width 68 is a width with the incision line 60 as a reference. In the example shown in FIG. 10, as an example of the incision width 68, the width incised from the incision line 60 with a center 60A of the incision line 60 as a reference is shown by a broken line. The pointer 58 is displayed on the screen 66. The user 18 sets the incision width 68 for the rendering image 46 by operating the pointer 58 via the reception device 14 (here, for example, the mouse 22). For example, the user 18 sets the incision width 68 by using the mouse 22 to position the pointer 58 at the center 60A and then performing drag and drop. Specifically, the mouse 22 drags the center 60A to move and drop the pointer 58 in a direction away from the incision line 60 (in the example shown in FIG. 10, a direction perpendicular to the incision line 60 on the screen 66). The dropped position is set as one end of the incision width 68, and the position at which one end of the incision width 68 is mirrored through the incision line 60, that is, the position line-symmetrical with one end of the incision width 68 with respect to the incision line 60 is set as the other end of the incision width 68.

Here, an aspect example has been described in which the other end of the incision width 68 is also set by setting one end of the incision width 68, but a method of setting the incision width 68 is not limited to this. For example, a movement locus obtained by moving the pointer 58 to cross the incision line 60 may be set as the incision width 68, or the incision width 68 may be set in response to the instruction received by the keyboard 20. In addition, the incision width 68 is may be determined according to various conditions (for example, the type of organ) in addition to the instruction received by the reception device 14, and it suffices to satisfy the conditions given to the incision target.

Figure 11:
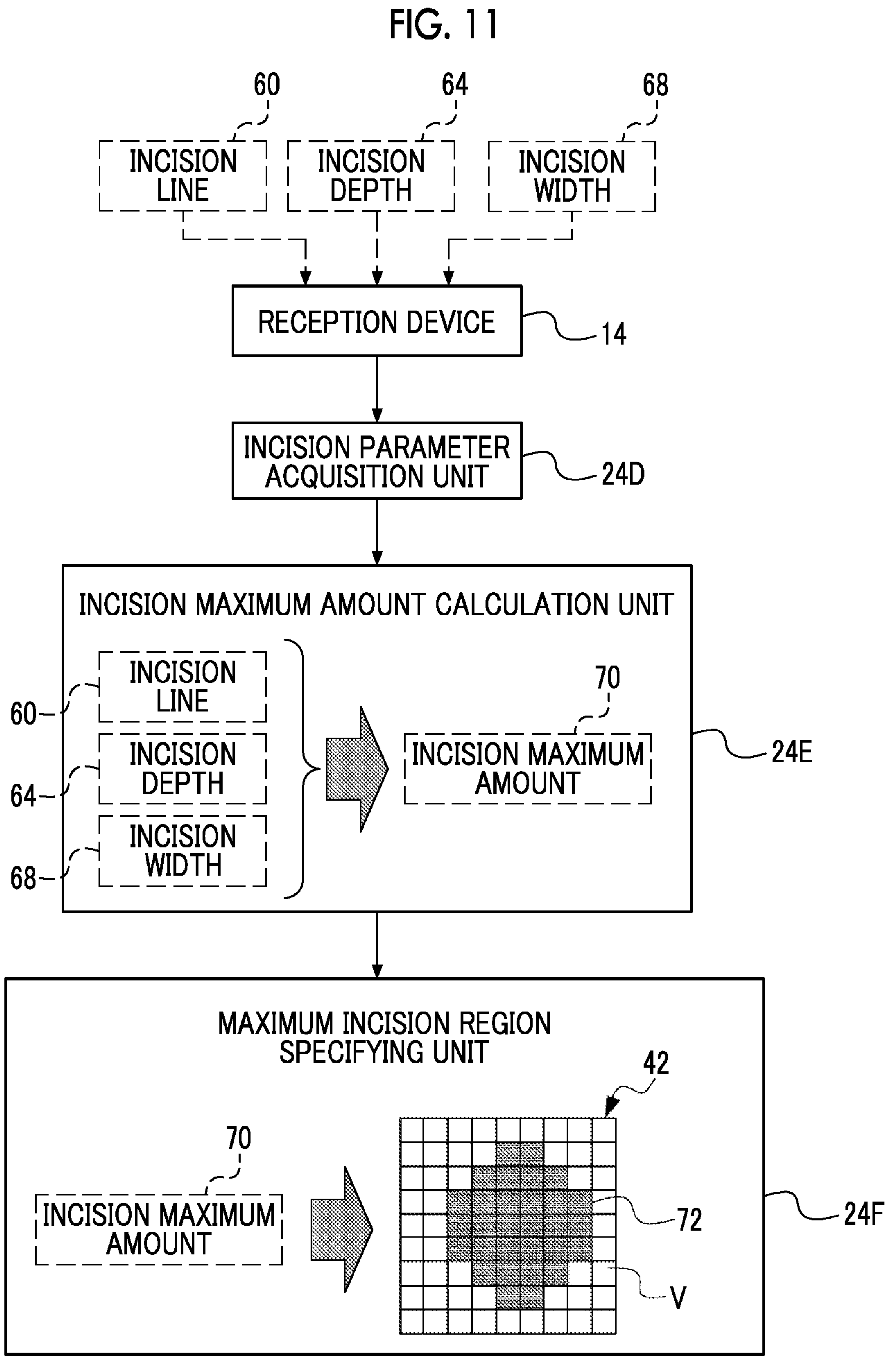
FIG. 11 is a conceptual diagram showing an example of processing contents of an incision parameter acquisition unit, an incision maximum amount calculation unit, and a maximum incision region specifying unit.

As shown in FIG. 11 as an example, the incision parameter acquisition unit 24D acquires the incision line 60, the depth 64, and the incision width 68 received by the reception device 14. In the following, for convenience of description, in a case in which the distinction is not necessary, the incision line 60, the depth 64, and the incision width 68 are also referred to as "incision parameters" without reference numerals.

The incision maximum amount calculation unit 24E calculates an incision maximum amount 70 based on the incision line 60, the depth 64, and the incision width 68 received by the incision parameter acquisition unit 24D. The incision maximum amount 70 is the size of the region incised (for example, an area of the incision region) of the three-dimensional organ image 42 (see FIGS. 4 to 7) according to the incision line 60, the depth 64, and the incision width 68. The incision maximum amount 70 is defined based on the incision line 60, the depth 64, and the incision width 68.

The incision maximum amount 70 is calculated by the incision maximum amount calculation unit 24E from an incision maximum amount arithmetic expression (not shown). The incision maximum amount arithmetic expression is an arithmetic expression in which the incision line 60, the depth 64, and the incision width 68 are used as independent variables, and the incision maximum amount 70 is used as a dependent variable. Note that, instead of the incision maximum amount arithmetic expression, the incision maximum amount 70 may be derived from an incision maximum amount table (not shown) in which the incision line 60, the depth 64, and the incision width 68 are used as input values, and the incision maximum amount 70 is used as the output value.

The maximum incision region specifying unit 24F specifies a maximum incision region 72 from the three-dimensional organ image 42 (see FIGS. 4 to 7) by using the incision maximum amount 70 calculated by the incision maximum amount calculation unit 24E. The maximum incision region 72 refers to a region in which the incision region 52 (FIG. 7) is maximized. Specifying the maximum incision region 72 means, for example, deciding the three-dimensional coordinate for specifying the position of the region in which the incision region 52 is maximized in the three-dimensional organ image 42. The three-dimensional coordinate for specifying the position of the region in which the incision region 52 is maximized in the three-dimensional organ image 42 is decided by the calculation according to the arithmetic expression in which the incision line 60, the depth 64, the incision width 68, the incision maximum amount 70, and the like are used as independent variable, and the three-dimensional coordinate for specifying the position of the outer edge of the region in which the incision region 52 is maximized in the three-dimensional organ image 42 are a dependent variable.

Figure 12:
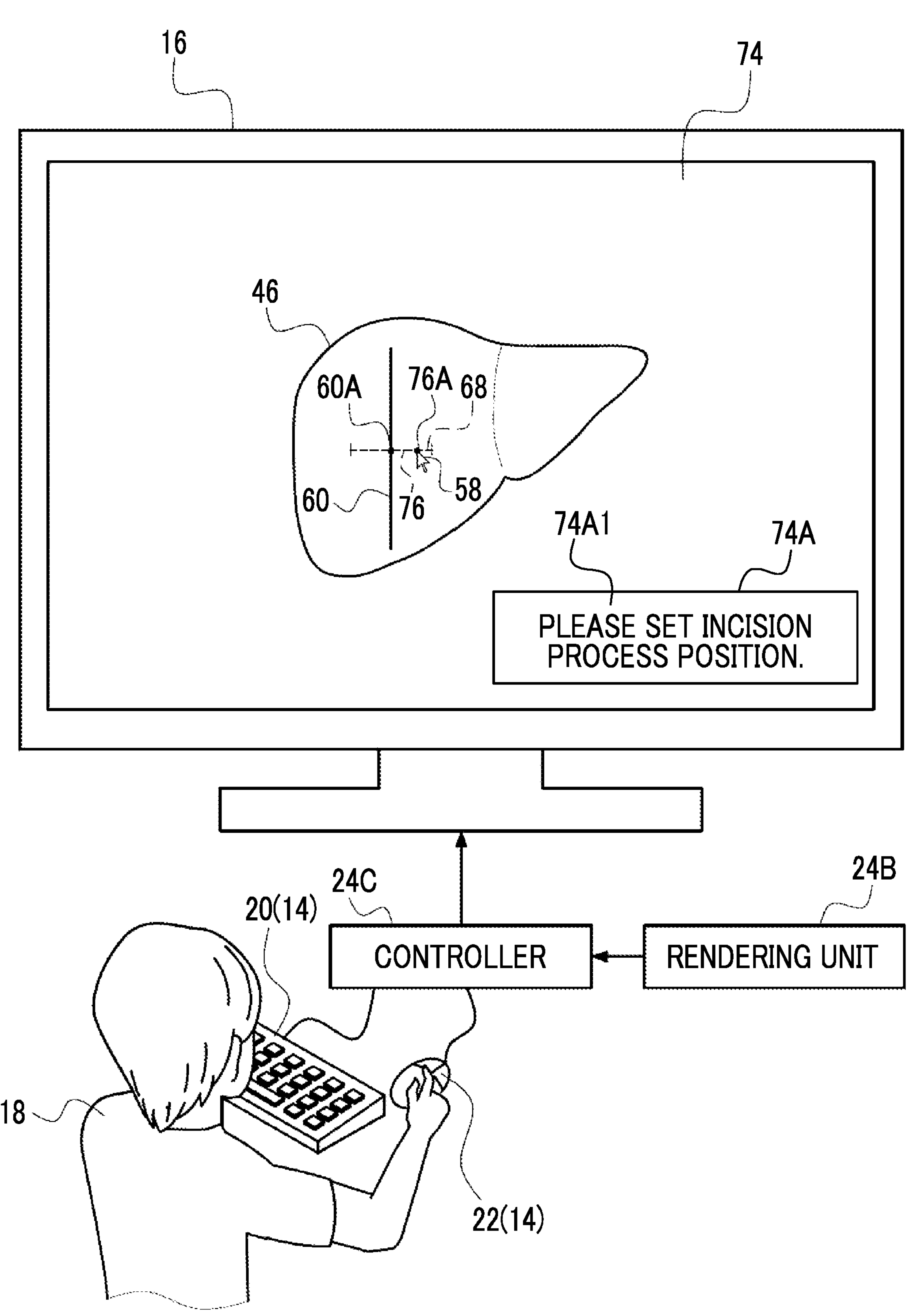
FIG. 12 is a conceptual diagram showing an example of an aspect in which an incision process position is set.

In a case in which specifying the maximum incision region by the maximum incision region specifying unit 24F is terminated, as shown in FIG. 12 as an example, the screen displayed on the display 16 by the controller 24C is switched from the screen 66 (see FIG. 10) to a screen 74. The screen 74 includes a guide message display region 74A. A guide message 74A1 is displayed in the guide message display region 74A. The guide message 74A1 is a message that guides the user 18 to set an incision process position 76A for the three-dimensional organ image 42 (see FIGS. 4 to 7) via the rendering image 46. The incision process position 76A refers to a position between the incision line 60 and the maximum incision region 72, that is, a position passed during the incision process from the incision line 60 to the maximum incision region 72. In the example shown in FIG. 12, a message "Please set the incision process position." is shown as an example of the guide message 74A1.

An incision width line 76 (line of broken line in the example shown in FIG. 12) that crosses the incision line 60 on the center 60A is displayed on the screen 74 as a line that defines the incision width 68 on the rendering image 46. The incision process position 76A is set in response to the instruction received by the reception device 14. For example, in a case in which the user 18 aligns the pointer 58 with one point on the incision width line 76 using the mouse 22 and clicks, the position at which the pointer 58 is aligned is set as the incision process position 76A. Here, an aspect example has been described in which the incision process position 76A is set in response to the operation by the mouse 22, but the technology of the present disclosure is not limited to this, and the incision process position 76A may be set by operating the keyboard 20, the touch panel, and/or a tablet terminal. In addition, the incision process position 76A may be determined according to various conditions (for example, the type of organ) in addition to the instruction received by the reception device 14.

Figure 13:
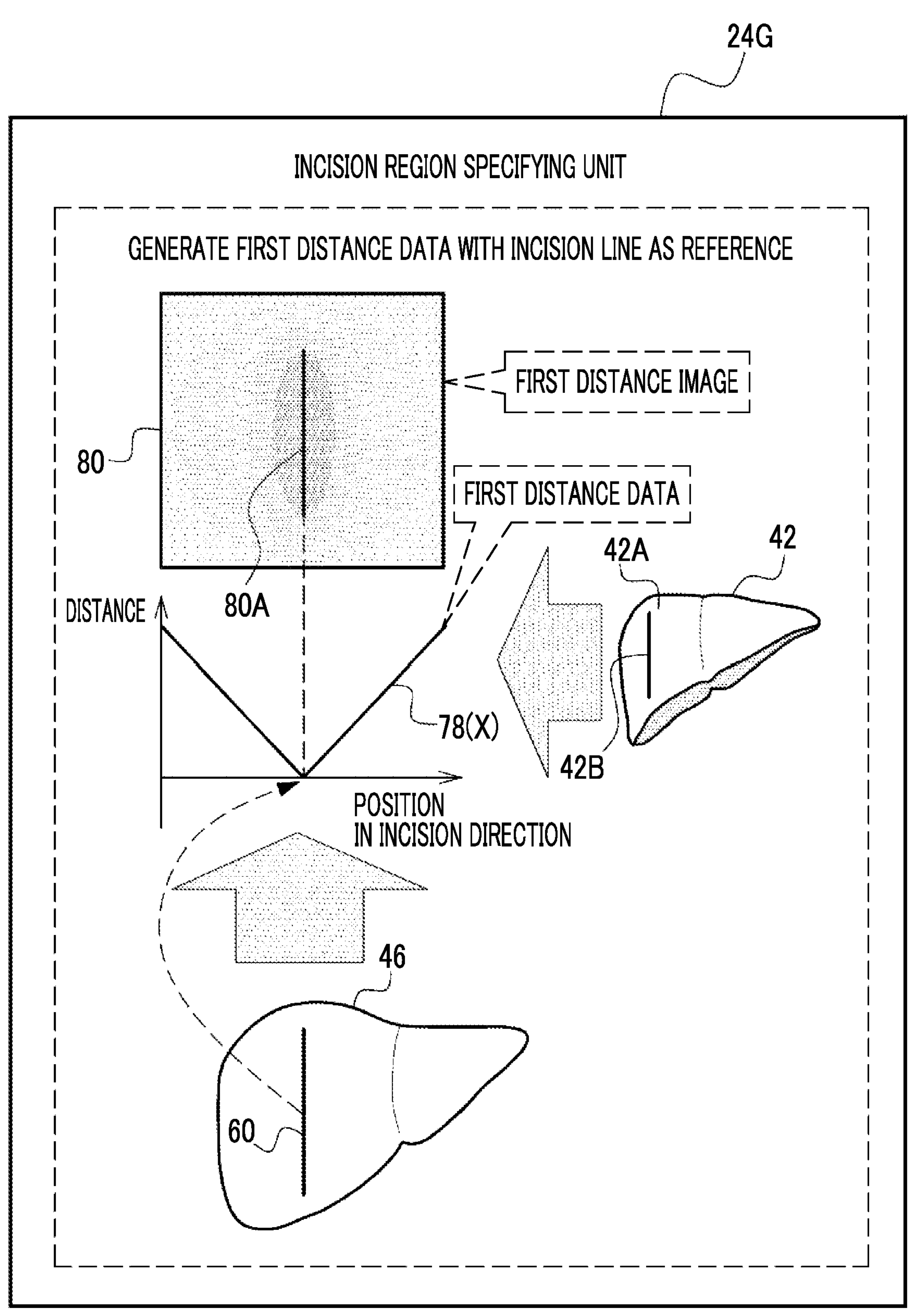
FIG. 13 is a conceptual diagram showing an example of a processing content in which first distance data is generated.

In a case in which the setting of the incision process position 76A is terminated, as shown in FIG. 13 as an example, the incision region specifying unit 24G generates, as one-dimensional data, first uniaxial distance data 78 which is the distance data with the incision line 60 as a reference. The three-dimensional organ image 42 includes a three-dimensional organ surface image 42A showing a surface of the organ.

Here, as the three-dimensional data, the distance data with the incision line 60 as a reference is referred to as first distance data X. The first distance data X is data indicating a distance from an organ image incision line 42B set for the three-dimensional organ surface image 42A via the rendering image 46. The organ image incision line 42B is a line set as a line corresponding to the incision line 60 for the three-dimensional organ surface image 42A via the rendering image 46.

Stated another way, the organ image incision line 42B corresponds to the smallest incision region defined based on the incision line 60 and the incision depth 64. In addition, the first distance data X is the three-dimensional data indicating the distance from the organ image incision line 42B for each voxel V constituting the three-dimensional organ image 42. Here, in the example shown in FIG. 13, an image in which, in the first distance data X, the first distance data X in the cross section orthogonal to the plane defined by the incision line 60 and the incision depth 64 is represented such that the image is darker as the distance from the organ image incision line 42B is closer is shown as a first distance image 80.

The first distance image 80 corresponds to the first distance data X on a surface corresponding to the three-dimensional organ surface image 42A. That is, the first distance image 80 is an image showing a distribution state of the first distance data X with an line 80A corresponding to the organ image incision line 42B on the three-dimensional organ surface image 42A as a reference. In addition, a line segment showing a position in a direction intersecting the organ image incision line 42B on the first distance image 80 (hereinafter referred to as a "first intersection direction position"), and a distance from the organ image incision line 42B for each first intersection direction position is indicated as in the first uniaxial distance data 78. The position corresponding to the organ image incision line 42B is indicated as "0" of a reference distance.

As indicated by the first uniaxial distance data 78, the first distance data X is increased as the distance from the organ image incision line 42B is away from the organ image incision line 42B in a direction of incised from the organ image incision line 42B (hereinafter, also referred to as an "incision direction").

Figure 14:
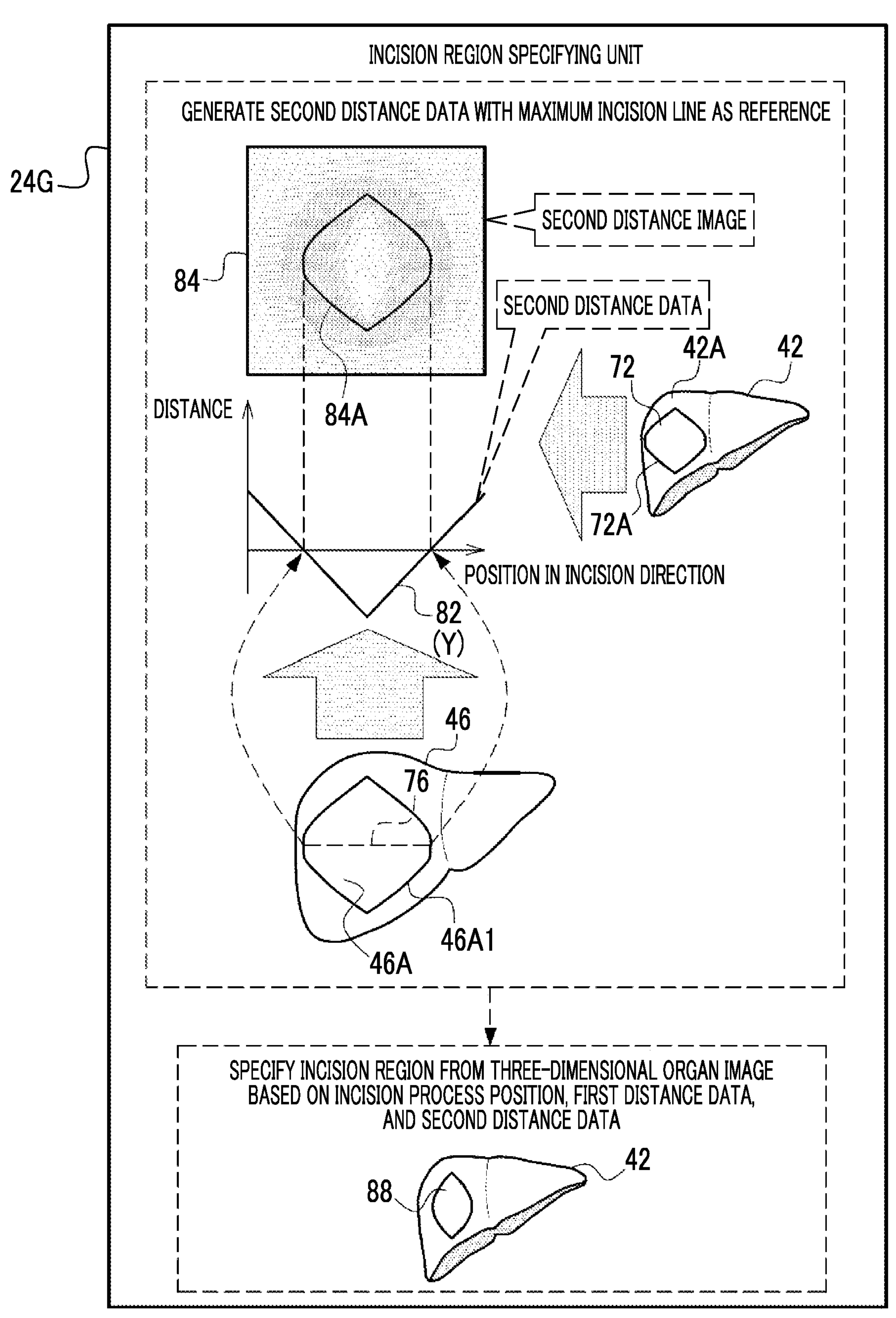
FIG. 14 is a conceptual diagram showing an example of a processing content in which second distance data is generated.

As shown in FIG. 14 as an example, the incision region specifying unit 24G generates, as the one-dimensional data, second uniaxial distance data 82, which is distance data with the maximum incision region 72 designated for the three-dimensional organ image 42, that is, the maximum incision region 72 specified by the maximum incision region specifying unit 24F as a reference.

Here, as the three-dimensional data, the distance data with the maximum incision region 72 as a reference is referred to as second distance data Y. The second distance data Y is data indicating a distance from the maximum incision region 72. In addition, the second distance data Y is the three-dimensional data indicating the distance from the maximum incision region 72 for each voxel V constituting the three-dimensional organ image 42. Here, in the example shown in FIG. 14, an image in which, in the second distance data Y, the second distance data Y in the cross section orthogonal to the plane defined by the incision line 60 and the incision depth 64 is represented such that the image is darker as the distance from the maximum incision region 72 is closer is shown as a second distance image 84.

The second distance image 84 corresponds to the second distance data Y on a surface corresponding to the three-dimensional organ surface image 42A. In addition, the second distance image 84 also shows a distance from an outer edge line 84A corresponding to the maximum incision region 72 on the three-dimensional organ surface image 42A. That is, the second distance image 84 is an image showing a distribution state of the second distance data Y with an outer edge line 72A as a reference.

The outer edge line 72A corresponds to an outer edge line 46A1 of an incision surface 46A determined according to the incision line 60 (see FIG. 8), the depth 64 (see FIG. 9), and the incision width 68 (see FIG. 10) set for the rendering image 46. In addition, a line segment showing a position in a direction intersecting the outer edge line 72A on the second distance image 84 (hereinafter referred to as a "second intersection direction position"), and a distance from the outer edge line 72A for each second intersection direction position is indicated as in the second uniaxial distance data 82. Note that, in the second uniaxial distance data 82, the position corresponding to the maximum incision region 72 (that is, the outer edge line 72A) is indicated as the reference distance "0".

The second distance data Y, that is, the data indicating the distance from the maximum incision region 72 is data representing the inside of the maximum incision region 72 in the three-dimensional organ image 42 by a negative value, and representing the outside of the maximum incision region 72 in the three-dimensional organ image 42 by a positive value. For example, a value of the distance indicated by the second uniaxial distance data 82 is decreased as the distance is away from the outer edge line 72A to the inside in the incision direction of the three-dimensional organ image 42, and is increased as the distance is away from the outer edge line 72A to the inside.

In the example shown in FIG. 14, in the outer edge line 72A, the position corresponding to one end of the incision width line 76 and the position corresponding to the other end of the incision width line 76 are the reference distance "0". In this case, the distance is increased to a negative side as the distance indicated by the second distance data Y is away from the position corresponding to one end of the incision width line 76 in the outer edge line 72A to the inside of the maximum incision region 72 in the incision direction of the three-dimensional organ image 42, and is increased to a positive side as the distance is away from the position corresponding to one end of the incision width line 76 in the outer edge line 72A to the outside of the maximum incision region 72 in the incision direction of the three-dimensional organ image 42. In addition, the distance is increased to a negative side as the distance indicated by the second distance data Y is away from the position corresponding to the other end of the incision width line 76 in the outer edge line 72A to the inside of the maximum incision region 72 in the incision direction of the three-dimensional organ image 42, and is increased to a positive side as the distance is away from the position corresponding to the other end of the incision width line 76 in the outer edge line 72A to the outside of the maximum incision region 72 in the incision direction of the three-dimensional organ image 42.

The incision region specifying unit 24G specifies an incision region 88 (see FIG. 15) from the three-dimensional organ image 42 based on the incision process position 76A (see FIG. 12), the first distance data X, and the second distance data Y.

As shown in FIG. 15 as an example, the incision region specifying unit 24G calculates third distance data Z as the three-dimensional data based on "D(0)" indicating the first distance data X, "D(1)" indicating the second distance data Y, and "α" which is a numerical value indicating the incision process position 76A. α is a value within a range in which a position of the organ image incision line 42B is set to a lower limit value "0" and a position of the maximum incision region (that is, the outer edge line 72A) (see FIG. 14) is set to an upper limit value "1". The third uniaxial distance data 86 is data obtained by interpolating the first uniaxial distance data 78 and the second uniaxial distance data 82. For example, the third uniaxial distance data 86 is calculated from Expression (1). In Expression (1), D(α) indicates the third uniaxial distance data 86.

$$D(\alpha)=(1-\alpha)D(0)+\alpha D(1) \quad (1)$$

The third distance data Z is data indicating a distance for each position in the incision direction. A position at which the distance indicated by the third distance data Z is "0" is a position corresponding to the incision process position 76A of the incision width line 76.

In addition, the third distance data Z corresponds to the three-dimensional data indicating a distance from the incision region 88 in a case in which the incision is made at the incision process position 76A for each voxel V constituting the three-dimensional organ surface image 42A. Here, in the example shown in FIG. 15, an image in which, in the third distance data Z, the third distance data Z in the cross section orthogonal to the plane defined by the incision line 60 and the incision depth 64 is represented such that the image is darker as the distance from the incision region 88 is closer is shown as a third distance image 90. Stated another way, the third distance image 90 corresponds to the third distance data Z on the surface corresponding to the three-dimensional organ surface image 42A.

In addition, the third distance image 90 shows a distance from the outer edge line 88A of the incision region 88 on the three-dimensional organ surface image 42A. The third distance image 90 is an image showing a distribution state of the third distance data Z with the outer edge line 90A corresponding to the incision region 88 on the three-dimensional organ surface image 42A as a reference. In addition, a line segment showing a position in a direction intersecting an outer edge line 88A on the third distance image 90 (hereinafter referred to as a "third intersection direction position"), and a distance from the outer edge line 88A for each third intersection direction position is indicated as in the third uniaxial distance data 86. Note that, in the third uniaxial distance data 86, the position corresponding to the incision region 88 (that is, the outer edge line 88A) is indicated as the reference distance "0".

In addition, the third distance data Z is data representing the distance from the incision process position 76A on the incision width line 76 to the position on the incision line 60 side by a negative value, and representing the distance from the incision process position 76A on the incision width line 76 to the position on the opposite side to the incision line 60 by a positive value. A value of the distance indicated by the third distance data Z is decreased as the distance is away from the incision process position 76A to the incision line 60 side in the incision direction of the three-dimensional organ image 42, and is increased as the distance is away from the incision process position 76A to the opposite side of the incision line 60.

The incision region specifying unit 24G specifies the incision region 88 based on the third distance data Z. Specifying the incision region 88 refers to specifying the three-dimensional coordinates of a plurality of the voxels V (see FIGS. 6, 7, and 11) constituting the incision region 88. The outer edge line 90A of the third distance image 90 corresponds to the outer edge line 88A of the incision region 88. The position of the voxel V inside the outer edge line 88A is specified from the third distance data Z inside the region surrounded by the outer edge line 90A in the third distance image 90.

Figure 16:
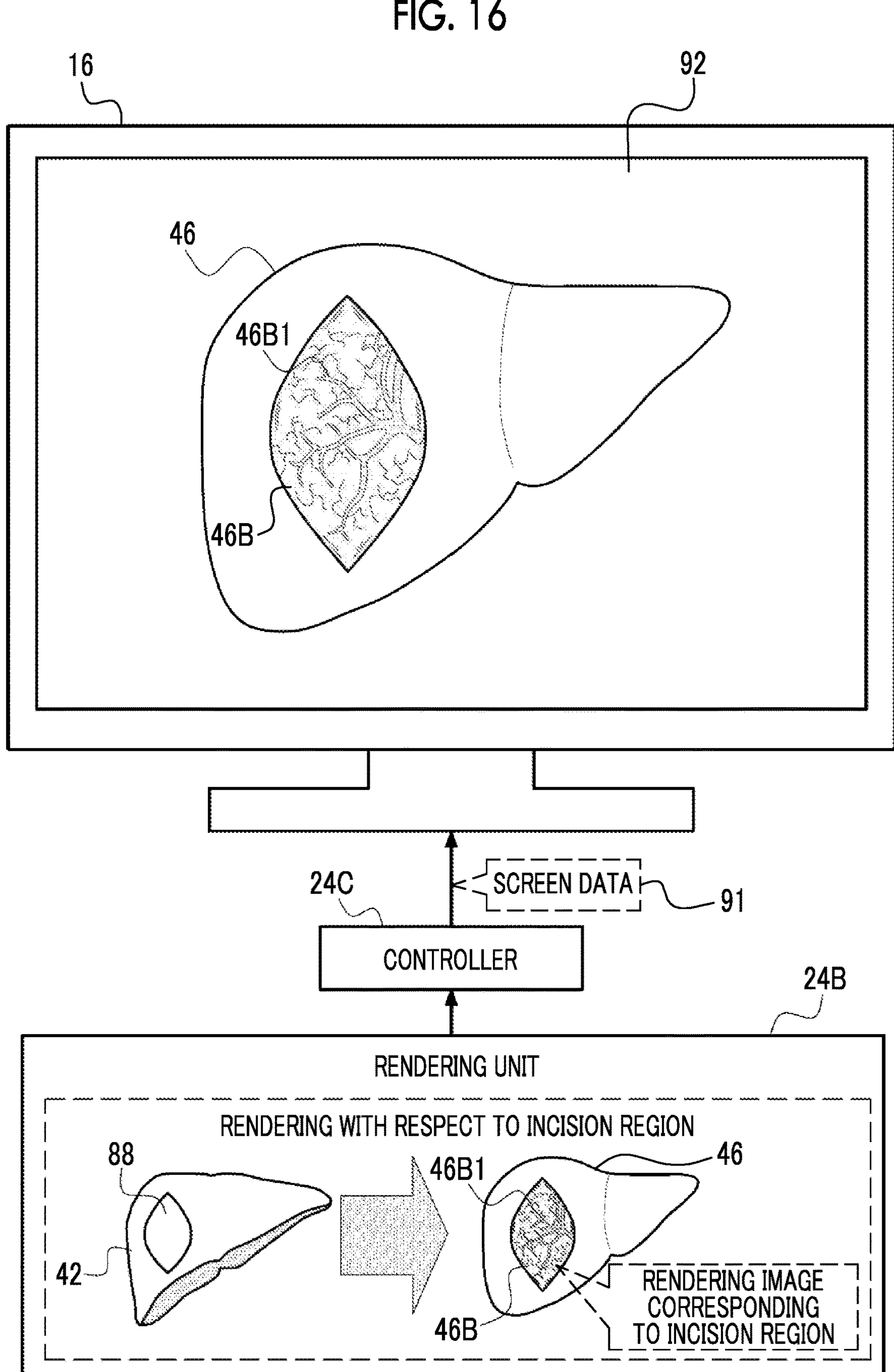
FIG. 16 is a screen view showing an example of an aspect in which a rendering image including an incision region rendering image is displayed on a display.

In a case in which the incision region 88 is specified by the incision region specifying unit 24G, the rendering unit 24B performs rendering with respect to the incision region 88 as shown in FIG. 16 as an example. That is, the rendering unit 24B skips rendering in the maximum incision region 72, and performs rendering with respect to the incision region 88 at a timing when the incision region 88 is specified by the incision region specifying unit 24G. As a result, an incision region rendering image 46B1, which is a rendering image corresponding to the incision region 88, is generated in the incision region 46B corresponding to the position of the incision region 88 of the rendering image 46. Note that skipping rendering in the maximum incision region 72 means that rendering is not performed with respect to the maximum incision region 72.

The controller 24C generates screen data 91 for displaying the rendering image 46 including the incision region rendering image 46B1 on the display 16, and outputs the generated screen data 91 to the display 16. Here, the screen data 91 is an example of "data" according to the technology of the present disclosure.

In the example shown in FIG. 16, the screen data 91 is data indicating a screen 92. The screen data 91 is input to the display 16 by the controller 24C, and the screen 92 indicated by the screen data 91 is displayed. The rendering image 46 including the incision region rendering image 46B1 is displayed on the screen 92.

Next, an action of the medical service support device 10 will be described with reference to FIG. 17.

Figure 17:
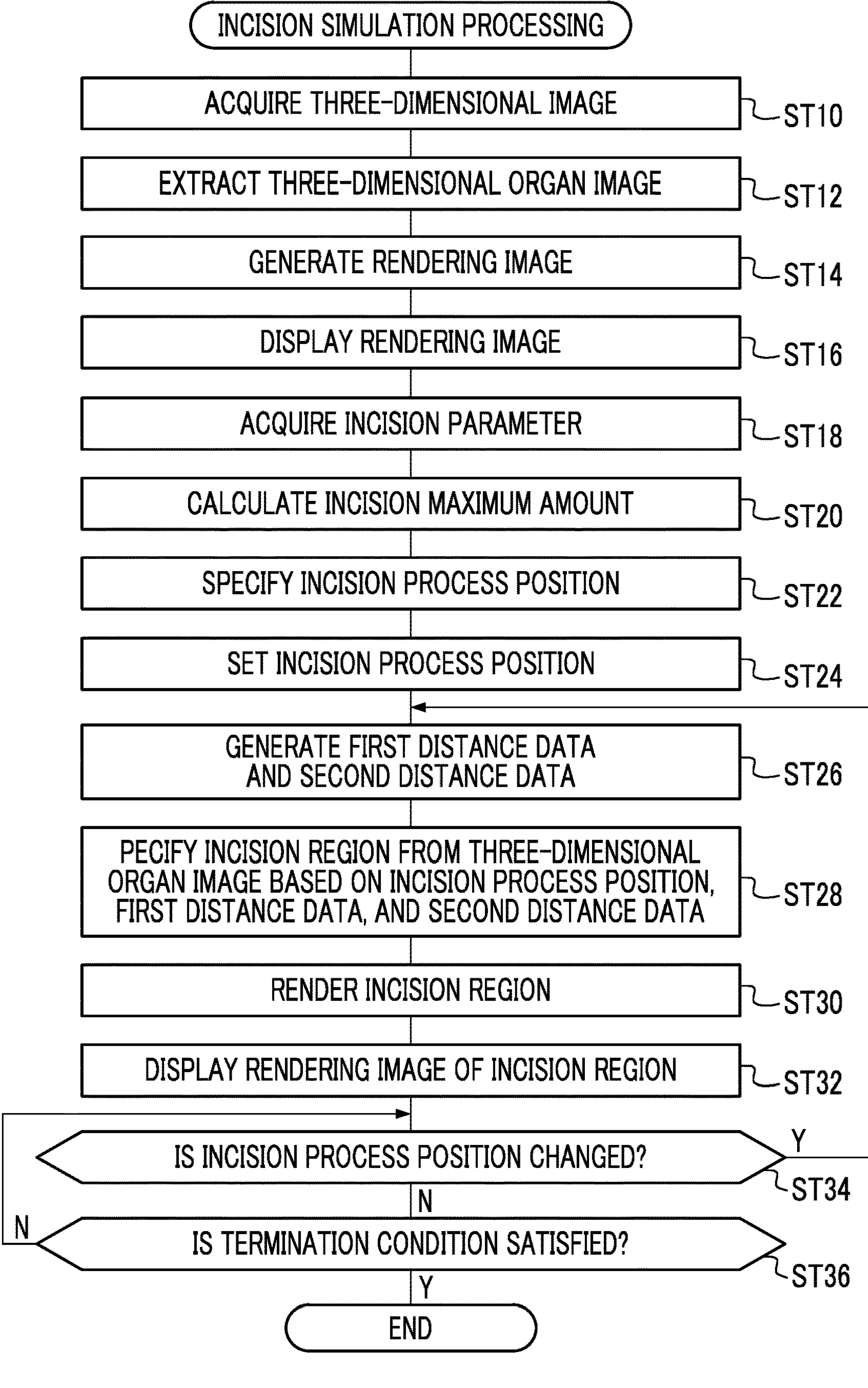
FIG. 17 is a flowchart showing an example of a flow of incision simulation processing.

FIG. 17 shows an example of a flow of incision simulation processing performed by the processor 24. Note that the flow of the incision simulation processing shown in FIG. 17 is an example of an "incision simulation method" according to the technology of the present disclosure.

In the incision simulation processing shown in FIG. 17, first, in step ST10, the extraction unit 24A acquires the three-dimensional image 38 from the storage 26 (see FIG. 4). After the processing of step ST10 is executed, the incision simulation processing proceeds to step ST12.

In step ST12, the extraction unit 24A extracts the three-dimensional organ image 42 from the three-dimensional image 38 acquired in step ST10 (see FIG. 4). After the processing of step ST12 is executed, the incision simulation processing proceeds to step ST14.

Figure 5:
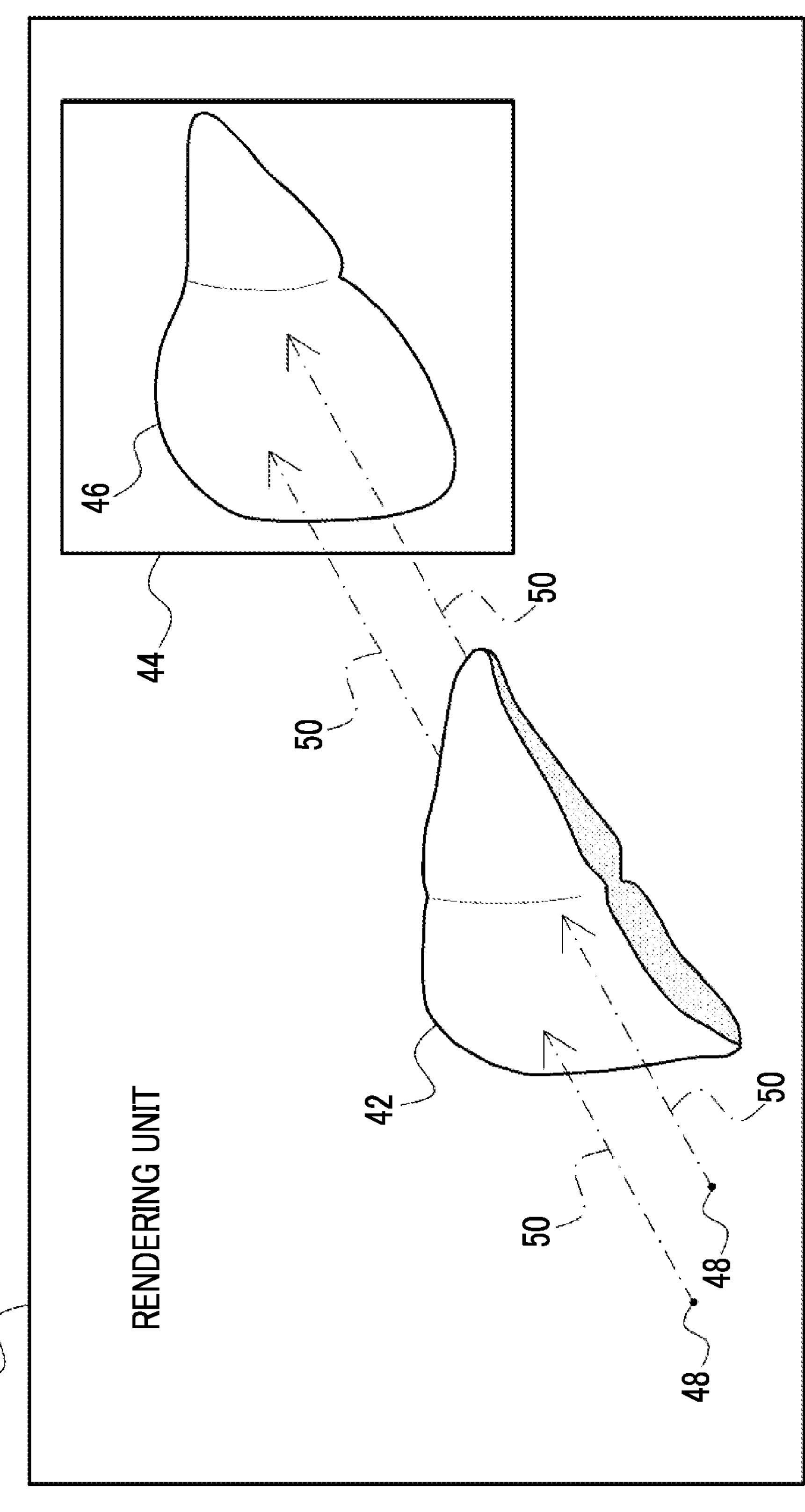
FIG. 5 is a conceptual diagram showing an example of a processing content of a rendering unit.

In step ST14, the rendering unit 24B generates the rendering image 46 by performing rendering with respect to the three-dimensional organ image 42 extracted in step ST12 (see FIGS. 5 and 6). After the processing of step ST14 is executed, the incision simulation processing proceeds to step ST16.

In step ST16, the controller 24C displays the rendering image 46 generated in step ST14 on the display 16 (see FIGS. 8 to 10). After the processing of step ST16 is executed, the incision simulation processing proceeds to step ST18.

In step ST18, the incision parameter acquisition unit 24D acquires the incision parameters (that is, the incision line 60, the depth 64, and the incision width 68) received by the reception device 14 (see FIG. 11). After the processing of step T18 is executed, the incision simulation processing proceeds to step ST20.

In step ST20, the incision maximum amount calculation unit 24E calculates the incision maximum amount 70 based on the incision parameters acquired in step ST18 (see FIG. 11). After the processing of step ST20 is executed, the incision simulation processing proceeds to step ST22.

In step ST22, the maximum incision region specifying unit 24F specifies the maximum incision region 72 from the three-dimensional organ image 42 extracted in step ST12 by using the incision maximum amount 70 calculated in step ST20 (see FIG. 11). After the processing of step ST22 is executed, the incision simulation processing proceeds to step ST24.

In step ST24, the controller 24C sets the incision process position 76A in response to the instruction received by the reception device 14 (see FIG. 12). After the processing of step ST24 is executed, the incision simulation processing proceeds to step ST26.

In step ST26, the incision region specifying unit 24G generates the first distance data X with the incision line 60 included in the incision parameters acquired in step ST18 as a reference (see FIG. 13), and generates the second distance data Y with the maximum incision region 72 specified in step ST22 as a reference (see FIG. 14). After the processing of step ST26 is executed, the incision simulation processing proceeds to step ST28.

In step ST28, the incision region specifying unit 24G specifies the incision region 88 from the three-dimensional organ image 42 extracted in step ST12 based on the incision process position 76A set in step ST24, the first distance data X generated in step ST26, and the second distance data Y generated in step ST26 (FIGS. 14 and 15). After the processing of step ST28 is executed, the incision simulation processing proceeds to step ST30.

In step ST30, the rendering unit 24B generates the incision region rendering image 46B1 by performing rendering with respect to the incision region 88 specified in step ST28. After the processing of step ST30 is executed, the incision simulation processing proceeds to step ST32.

In step ST32, the controller 24C displays the rendering image 46 including the incision region rendering image 46B1 generated in step ST30 on the display 16. After the processing of step ST32 is executed, the incision simulation processing proceeds to step ST34.

In step ST34, the incision region specifying unit 24G determines whether or not the incision process position 76A is changed. In a case in which the incision process position 76A is changed in step ST34, a positive determination is made, and the incision simulation processing proceeds to step ST26. In a case in which the incision process position 76A is not changed in step ST34, a negative determination is made, and the incision simulation processing proceeds to step ST36.

In step ST36, the incision region specifying unit 24G determines whether or not a condition for terminating the incision simulation processing (hereinafter referred to as a "termination condition") is satisfied. As an example of the termination condition, there is a condition that an instruction for terminating the incision simulation processing is received by the reception device 14. In a case in which the termination condition is not satisfied in step ST36, a negative determination is made, and the incision simulation processing proceeds to step ST34. In a case in which the termination condition is satisfied in step ST38, a positive determination is made, and the incision simulation processing is terminated.

As described above, in the medical service support device 10, the incision region 88 is specified from the three-dimensional organ image 42 based on the incision process position 76A, the first distance data X, and the second distance data Y. Therefore, with the present configuration, it is possible to reduce the load on the operation relating to the incision region 88 (see FIGS. 14 to 16) as compared to a case in which the operation (for example, the operation relating to the blank region 54 shown in FIG. 11) relating to the incision region 52 (see FIG. 7) is followed and executed as the incision region 52 of the three-dimensional organ image 42 is gradually expanded.

In addition, in the medical service support device 10, the three-dimensional image 38 is acquired from the storage 26 by the extraction unit 24A, and the three-dimensional organ image 42 is extracted from the three-dimensional image 38. Moreover, the incision region 88 is specified from the three-dimensional organ image 42 extracted by the extraction unit 24A based on the incision process position 76A, the first distance data X, and the second distance data Y. Therefore, with the present configuration, it is possible to reduce the load on the operation relating to the incision region 88 (see FIGS. 14 to 16) of the three-dimensional organ image 42 extracted from the three-dimensional image 38 as compared to a case in which the operation relating to the incision region 52 (see FIG. 7) is followed and executed as the incision region 52 of the three-dimensional organ image 42 extracted from the three-dimensional image 38 is gradually expanded.

In addition, in the medical service support device 10, the incision line 60 received by the reception device 14 is acquired by the incision parameter acquisition unit 24D. Moreover, the first distance data X with the incision line 60 as a reference is generated. Therefore, with the present configuration, it is possible to easily obtain the first distance data X with the incision line 60 intended by the user 18 as a reference as compared to a case in which the incision line 60 is fixed.

In addition, in the medical service support device 10, the maximum incision region 72 is specified from the three-dimensional organ image 42 by using the incision maximum amount 70 set for the three-dimensional organ image 42. Therefore, with the present configuration, it is possible to specify the maximum incision region 72 with higher accuracy as compared to a case in which the maximum incision region 72 is specified by using only a value independent to the incision maximum amount 70.

In addition, in the medical service support device 10, the incision maximum amount 70 is defined based on the incision line 60, the depth 64, and the incision width 68. Therefore, with the present configuration, it is possible to define the incision maximum amount 70 with higher accuracy as compared to a case in which the incision maximum amount 70 is defined without using any of the incision line 60, the depth 64, or the incision width 68.

In addition, in the medical service support device 10, the incision width 68 received by the reception device 14 is acquired by the incision parameter acquisition unit 24D. Therefore, with the present configuration, it is possible to facilitate setting of the incision width 68 intended by the user 18 as compared to a case in which the incision width 68 is fixed.

In addition, in the medical service support device 10, the data indicating the distance from the organ image incision line 42B set for the three-dimensional organ surface image 42A is used as the first distance data X. Therefore, with the present configuration, it is possible to specify the incision region 88 with higher accuracy as compared to a case in which the first distance data X is data completely independent to the data indicating the distance from the organ image incision line 42B set for the three-dimensional organ surface image 42A.

In addition, in the medical service support device 10, the data indicating the distance of the maximum incision region 72 from the outer edge line 72A is used as the second distance data Y. Therefore, with the present configuration, it is possible to specify the incision region 88 with higher accuracy as compared to a case in which the second distance data Y is data completely independent to the data indicating the distance of the maximum incision region 72 from the outer edge line 72A.

In addition, in the medical service support device 10, the data representing the inside of the maximum incision region 72 by a negative value and representing the outside of the maximum incision region 72 by a positive value is used as the data indicating the distance from the outer edge line 72A. Note that the inside of the maximum incision region 72 may be represented by a positive value, and the outside of the maximum incision region 72 may be represented by a negative value. Therefore, with the present configuration, it is possible to easily specify the inside and the outside of the maximum incision region 72 as compared to a case in which the data indicating the distance from the outer edge line 72A is the data, which is always represented by a positive value or a negative value independently of the inside and the outside of the maximum incision region 72.

In addition, in the medical service support device 10, the incision region 88 is specified based on the data obtained by interpolating the first distance data X and the second distance data Y. Therefore, with the present configuration, it is possible to reduce the operation load required for specifying the final incision region 88 (see FIGS. 14 to 16) as compared to a case in which the incision region 52 (see FIG. 7) is gradually expanded.

In addition, in the medical service support device 10, rendering is performed with respect to the incision region 88 at the timing when the incision region 88 is specified. Therefore, with the present configuration, it is possible to reduce the operation load on rendering as compared to a case in which rendering is always performed in the incision region 52 following the gradual expansion of the incision region 52 (see FIG. 7).

In addition, in the medical service support device 10, the rendering image 46 including the incision region rendering image 46B1 is displayed on the display 16. Therefore, with the present configuration, it is possible for the user 18 to visually grasp an aspect in the incision region 88.

Further, in the medical service support device 10, rendering with respect to the maximum incision region 72 (see FIG. 14) is skipped. Therefore, with the present configuration, it is possible to reduce the operation load as compared to a case in which the rendering operation is performed with respect to the maximum incision region 72.

Note that, in the embodiment described above, the aspect example has been described in which the first distance image 80, the second distance image 84, and the third distance image 90 are generated by the incision region specifying unit 24G, but the technology of the present disclosure is not limited to this, and the technology of the present disclosure is established even in a case in which the first distance image 80, the second distance image 84, and the third distance image 90 are generated. That is, it suffices that the third distance data Z is generated based on the first distance data X and the second distance data Y, and the incision region 88 is specified by using the third distance data Z.

In addition, in the embodiment described above, the aspect example has been described in which the incision simulation processing is performed by the processor 24 of the image processing device 12 provided in the medical service support device 10, but the technology of the present disclosure is not limited to this, and the device that performs the incision simulation processing may be provided outside the medical service support device 10.

Figure 18:
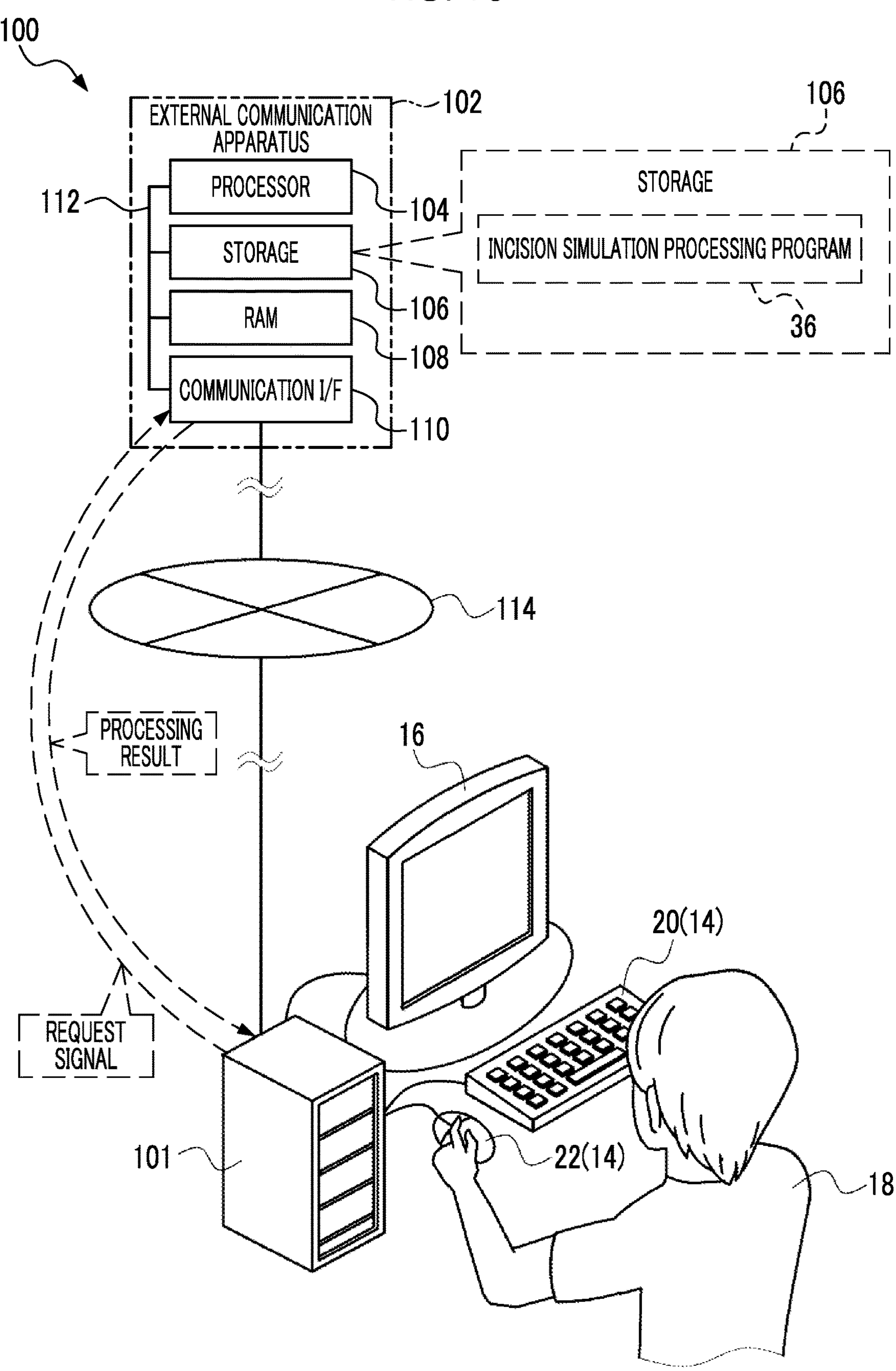
FIG. 18 is a conceptual diagram showing a schematic configuration of a medical service support system.

In this case, as shown in FIG. 18 as an example, it suffices to use a medical service support system 100. The medical service support system 100 comprises an information processing apparatus 101 and an external communication apparatus 102. The information processing apparatus 101 is an apparatus in which the incision simulation processing program 36 is removed from the storage 26 of the image processing device 12 provided in the medical service support device 10 described in the embodiment described above. The external communication apparatus 102 is, for example, a server. The server is realized, for example, by a main frame. Here, the main frame is described as an example, but this is merely an example, and the server may be realized by cloud computing, or may be realized by a network, such as fog computing, edge computing, or grid computing. Here, the server is described as an example of the external communication apparatus 102, but this is merely an example, and at least one personal computer or the like may be used as the external communication apparatus 102 instead of the server.

The external communication apparatus 102 comprises a processor 104, a storage 106, a RAM 108, and a communication I/F 110, and the processor 104, the storage 106, the RAM 108, and the communication I/F 110 are connected by a bus 112. The communication I/F 110 is connected to the information processing apparatus 101 via a network 114. The network 114 is, for example, the Internet. Note that the network 114 is not limited to the Internet, but may be a WAN and/or a LAN, such as an intranet.

The incision simulation processing program 36 is stored in the storage 106. The processor 104 executes the incision simulation processing program 36 on the RAM 108. The processor 104 performs the incision simulation processing described above according to the incision simulation processing program 36 executed on the RAM 108.

The information processing apparatus 101 transmits a request signal for requesting the external communication apparatus 102 to execute the incision simulation processing. The communication I/F 110 of the external communication apparatus 102 receives the request signal via the network 114. The processor 104 performs the incision simulation processing according to the incision simulation processing program 36, and transmits a processing result to the information processing apparatus 101 via the communication I/F 110. The information processing apparatus 101 receives the processing result transmitted from the external communication apparatus 102 (for example, a processing result by the incision region specifying unit 24G and/or the screen data 91) by the communication I/F 30 (see FIG. 2), and outputs the received processing result to various devices, such as the display 16.

Note that, in the example shown in FIG. 18, the external communication apparatus 102 is an example of an "incision simulation device" according to the technology of the present disclosure, and the processor 104 is an example of a "processor" according to the technology of the present disclosure.

In addition, the incision simulation processing may be performed in a distributed manner by a plurality of devices including the information processing apparatus 101 and the external communication apparatus 102.

In addition, in the embodiment described above, the aspect example has been described in which the processor 24 is realized by the CPU and the GPU, but the technology of the present disclosure is not limited to this, and the processor 24 may be a processor realized by at least one CPU, at least one GPU, at least one general-purpose computing on graphics processing units (GPGPU), and/or at least one tensor processing unit (TPU).

In addition, in the embodiment described above, the aspect example has been described in which the incision simulation processing program 36 is stored in the storage 26, but the technology of the present disclosure is not limited to this. For example, as shown in FIG. 19, the incision simulation processing program 36 may be stored in a storage medium 116, such as an SSD or a USB memory. The storage medium 116 is a portable non-transitory storage medium. The incision simulation processing program 36 stored in the storage medium 116 is installed in the image processing device 12 of the medical service support device 10. The processor 24 executes the incision simulation processing according to the incision simulation processing program 36.

In addition, the incision simulation processing program 36 may be stored in a storage device, such as another computer or server device, connected to the medical service support device 10 via a network (not shown), and the incision simulation processing program 36 may be downloaded in response to a request of the medical service support device 10 and installed in the image processing device 12.

It is not necessary to store all of the incision simulation processing program 36 in the storage device, such as another computer or server device, connected to the medical service support device 10, or the storage 26, and a part of the incision simulation processing program 36 may be stored. Note that the storage medium 116, the storage device, such as another computer or server device, connected to the medical service support device 10, and other external storages (for example, a database) are positioned as a memory which is directly or indirectly connected to the processor 24 and used.

In addition, in the embodiment described above, the image processing device 12 is described as the computer, but the technology of the present disclosure is not limited to this, and instead of the computer, a device including an application specific integrated circuit (ASIC), a field-programmable gate array (FPGA), and/or a programmable logic device (PLD) may be applied. In addition, instead of the computer, a hardware configuration and a software configuration may be used in combination.

The following various processors can be used as a hardware resource for executing the incision simulation processing described in the embodiment described above. Examples of the processor include the CPU, which is a general-purpose processor that functions as software, that is, a hardware resource for executing the incision simulation processing by executing the program. In addition, examples of the processor include a dedicated electric circuit which is a processor having a circuit configuration specially designed for executing specific processing, such as an FPGA, a PLD, or an ASIC. A memory is also built in or connected to each processor, and each processor executes the incision simulation processing by using the memory.

The hardware resource for executing the incision simulation processing may be configured by one of the various processors, or may be a combination of two or more processors of the same type or different types (for example, a combination of a plurality of FPGAs or a combination of a CPU and an FPGA). In addition, the hardware resource for executing the incision simulation processing may be one processor.

Examples of the configuration with one processor include, first, an aspect in which one processor is configured by a combination of one or more CPUs and software, and this processor functions as the hardware resource for executing the incision simulation processing. Second, as represented by a system-on-a-chip (SoC), there is an aspect in which a processor that realizes the functions of the entire system including a plurality of hardware resources that execute the incision simulation processing with a single integrated circuit (IC) chip is used. As described above, the incision simulation processing is realized by using one or more of the various processors described above as the hardware resource.

Further, as the hardware structures of these various processors, more specifically, an electric circuit in which circuit elements, such as semiconductor elements, are combined can be used. In addition, the incision simulation processing described above is merely an example. Therefore, it is needless to say that unnecessary steps may be deleted, new steps may be added, or the processing order may be changed within a range that does not deviate from the gist.

The contents described and shown above are the detailed description of the parts according to the technology of the present disclosure, and are merely examples of the technology of the present disclosure. For example, the above description of the configuration, the function, the action, and the effect is the description of examples of the configuration, the function, the action, and the effect of the parts according to the technology of the present disclosure. Therefore, it is needless to say that unnecessary parts may be deleted, new elements may be added, or replacements may be made with respect to the contents described and shown above within a range that does not deviate from the gist of the technology of the present disclosure. In addition, in order to avoid complications and facilitate understanding of the parts according to the technology of the present disclosure, in the contents described and shown above, the description of common technical knowledge and the like that do not particularly require description for enabling the implementation of the technology of the present disclosure are omitted.

In the present specification, “A and/or B” is synonymous with “at least one of A or B”. That is, “A and/or B” means that it may be only A, only B, or a combination of A and B. In addition, in the present specification, in a case in which three or more matters are associated and represented by “and/or”, the same concept as “A and/or B” is applied.

All of the documents, the patent applications, and the technical standards described in the present specification are incorporated in the present specification by referring to the same extent as a case in which individual document, patent application, and technical standard are specifically and individually noted to be incorporated by reference.

EXPLANATION OF REFERENCES

10: medical service support device
12: image processing device
14: reception device
16: display
18: user
20: keyboard
22: mouse
24, 104: processor
24A: extraction unit
24B: rendering unit
24C: controller
24D: incision parameter acquisition unit
24E: incision maximum amount calculation unit
24F: maximum incision region specifying unit
24G: incision region specifying unit
26, 106: storage
28, 108: RAM
30, 110: communication I/F
32: external I/F
34, 112: bus
36: incision simulation processing program
38: three-dimensional image
40: two-dimensional slice image
42: three-dimensional organ image
44: projection plane
46: rendering image
46B, 52, 88: incision region
46B1: incision region rendering image
48: viewpoint
50: ray
54: blank region
56, 62, 66, 74: screen
56A, 66A, 74A: guide message display region
56A1, 62A1, 66A1, 74A1: guide message
58: pointer
60: incision line
60A: center
62A: depth setting box
62A2: input box
62A3: confirmation key
68: incision width
70: incision maximum amount
72: maximum incision region
72A, 88A: outer edge line
76: incision width line
76A: incision process position
78: first uniaxial distance data
80: first distance image
80A, 84A: line
82: second uniaxial distance data
84: second distance image
86: third uniaxial distance data
90: third distance image
91: screen data
100: medical service support system
101: information processing apparatus
102: external communication apparatus
114: network
116: storage medium
V: voxel
X: first distance data
Y: second distance data
Z: third distance data

What is claimed is:

1. An incision simulation device comprising:

a processor, wherein the processor acquires an incision line for a three-dimensional organ image showing an organ which is an incision simulation target, specifies a maximum incision region from the three-dimensional organ image by using an incision maximum amount set for the three-dimensional organ image, specifies an incision process position within a range in which a position of the incision line is set to a lower limit and a position of the maximum incision region is set to an upper limit, specifies first distance data indicating a distance from the incision line set for a surface of the organ, specifies second distance data indicating a distance from an outer edge line of the maximum incision region, specifies third distance data by interpolating the first distance data and the second distance data according to the incision process position, specifies an incision region from the three-dimensional organ image based on the third distance data, and displays a rendering image of the organ generated with respect to the three-dimensional organ image and including an incision region rendering image generated in the incision region corresponding to a position of the incision region of the rendering image on a display.

2. The incision simulation device according to claim 1, wherein the processor acquires a three-dimensional image including the three-dimensional organ image, and extracts the three-dimensional organ image from the three-dimensional image.

3. The incision simulation device according to claim 1, wherein the processor acquires the incision line received by a reception device.

4. The incision simulation device according to claim 1, wherein the incision maximum amount is defined based on the incision line, an incision width with the incision line as a reference, and an incision depth set for the three-dimensional organ image.

5. The incision simulation device according to claim 4, wherein the processor acquires the incision width received by a reception device.

6. The incision simulation device according to claim 1, wherein the data indicating the distance from the outer edge line is data representing an inside of the maximum incision region in the three-dimensional organ image by one of a positive value and a negative value, and representing an outside of the maximum incision region in the three-dimensional organ image by the other of the positive value and the negative value.

7. The incision simulation device according to claim 1, wherein the processor performs volume rendering in the incision region at a timing when the incision region is specified.

8. The incision simulation device according to claim 1, wherein the processor outputs data for displaying the incision region rendering image obtained by performing volume rendering in the incision region on the display.

9. The incision simulation device according to claim 1, wherein the processor skips an operation of volume rendering in the maximum incision region.

10. An incision simulation method comprising:

acquiring an incision line for a three-dimensional organ image showing an organ which is an incision simulation target;

specifying a maximum incision region from the three-dimensional organ image by using an incision maximum amount set for the three-dimensional organ image;

specifying an incision process position within a range in which a position of the incision line is set to a lower limit and a position of the maximum incision region is set to an upper limit;

specifying first distance data indicating a distance from the incision line set for a surface of the organ;

specifying second distance data indicating a distance from an outer edge line of the maximum incision region;

specifying third distance data by interpolating the first distance data and the second distance data according to the incision process position;

specifying an incision region from the three-dimensional organ image based on the third distance data; and displaying a rendering image of the organ generated with respect to the three-dimensional organ image and including an incision region rendering image generated in the incision region corresponding to a position of the incision region of the rendering image on a display.

11. A non-transitory computer readable recording medium storing a program causing a computer to execute a process comprising:

acquiring an incision line for a three-dimensional organ image showing an organ which is an incision simulation target;

specifying a maximum incision region from the three-dimensional organ image by using an incision maximum amount set for the three-dimensional organ image;

specifying an incision process position within a range in which a position of the incision line is set to a lower limit and a position of the maximum incision region is set to an upper limit;

specifying first distance data indicating a distance from the incision line set for a surface of the organ;

specifying second distance data indicating a distance from an outer edge line of the maximum incision region;

specifying third distance data by interpolating the first distance data and the second distance data according to the incision process position;

specifying an incision region from the three-dimensional organ image based the third distance data; and displaying a rendering image of the organ generated with respect to the three-dimensional organ image and including an incision region rendering image generated in the incision region corresponding to a position of the incision region of the rendering image on a display.

* * * * *